United States Patent
Yoshida et al.

(10) Patent No.: US 11,864,873 B2
(45) Date of Patent: Jan. 9, 2024

(54) INTRAORAL SENSING SYSTEM AND INTRAORAL SENSING METHOD

(71) Applicants: SEIKO HOLDINGS KABUSHIKI KAISHA, Tokyo (JP); Science Energy CO., LTD., Tokyo (JP)

(72) Inventors: Yoshifumi Yoshida, Tokyo (JP); Kotaro Maki, Tokyo (JP)

(73) Assignees: SEIKO GROUP CORPORATION, Tokyo (JP); SCIENCE ENERGY CO., LTD., Tokyo (JP)

( * ) Notice: Subject to any disclaimer, the term of this patent is extended or adjusted under 35 U.S.C. 154(b) by 316 days.

(21) Appl. No.: 17/194,937

(22) Filed: Mar. 8, 2021

(65) Prior Publication Data

US 2021/0282650 A1 Sep. 16, 2021

(30) Foreign Application Priority Data

Mar. 13, 2020 (JP) .................................. 2020-044445

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0008* (2013.01); *A61B 5/026* (2013.01);
(Continued)

(58) Field of Classification Search
CPC .............. A61B 5/02055; A61B 5/0008; A61B 5/02438; A61B 5/026; A61B 5/117;
(Continued)

(56) References Cited

U.S. PATENT DOCUMENTS 9,700,395 B2 * 7/2017 Hohlbein ............. A46B 11/001
9,877,700 B1 * 1/2018 Asch .................... A61B 8/4494
(Continued)

FOREIGN PATENT DOCUMENTS

JP       2003-070752 A      3/2003
JP       2005-192938 A      7/2005
(Continued)

OTHER PUBLICATIONS

Machine Translation of JP-2006309465-A by Fukuda S (Year: 2006).*

(Continued)

*Primary Examiner* — Carl H Layno
*Assistant Examiner* — Manolis Pahakis
(74) *Attorney, Agent, or Firm* — Crowell & Moring LLP

(57) ABSTRACT

The present intraoral sensing system which is configured to sense a biological information using a sensor module installed in an oral cavity, including a sensor module installed in an oral cavity of a patient and configured to store data acquired when the biological information is sensed, a storage configured to acquire the data and an identification information of the patient stored by the sensor module, associate the acquired data with the identification information of the patient, and store the association, a terminal apparatus for a dentist configured to analyze the data stored in the storage for each of the identification information of the patient, and a terminal apparatus for a doctor configured to acquire the data associated with a patient who has a developed disease among the data of patients stored in the storage, from the terminal apparatus for a dentist.

10 Claims, 10 Drawing Sheets

(51) Int. Cl.
*A61B 5/024* (2006.01)
*A61B 5/026* (2006.01)
*A61B 5/117* (2016.01)
*A61B 5/1455* (2006.01)
*H04Q 9/00* (2006.01)

(52) U.S. Cl.
CPC .......... *A61B 5/02438* (2013.01); *A61B 5/117* (2013.01); *A61B 5/14552* (2013.01); *A61B 5/4205* (2013.01); *A61B 5/4557* (2013.01); *A61B 5/682* (2013.01); *H04Q 9/00* (2013.01); *A61B 2560/0214* (2013.01); *A61B 2562/0219* (2013.01); *A61B 2562/0233* (2013.01); *A61B 2562/0247* (2013.01); *A61B 2562/0261* (2013.01); *A61B 2562/0271* (2013.01); *H04Q 2209/10* (2013.01); *H04Q 2209/40* (2013.01)

(58) Field of Classification Search
CPC . A61B 5/14552; A61B 5/4205; A61B 5/4557; A61B 5/682; A61B 2560/0214; A61B 2562/0219; A61B 2562/0233; A61B 2562/0247; A61B 2562/0261; A61B 2562/0271; H04Q 9/00; H04Q 2209/10; H04Q 2209/40; A61C 8/00
See application file for complete search history.

(56) References Cited

U.S. PATENT DOCUMENTS

| | | | | |
|---|---|---|---|---|
| 10,004,456 | B2* | 6/2018 | Mu | A61B 5/14503 |
| 10,470,847 | B2* | 11/2019 | Shanjani | H04B 5/0056 |
| 10,674,960 | B2* | 6/2020 | Fridman | A61B 5/228 |
| 11,432,768 | B2* | 9/2022 | Fridman | A61B 5/4277 |
| 2006/0116561 | A1* | 6/2006 | Tricca | A61B 5/0088 |
| | | | | 600/309 |
| 2010/0234793 | A1* | 9/2010 | Dacey, Jr. | A61B 5/14546 |
| | | | | 604/8 |
| 2013/0253286 | A1* | 9/2013 | Fridman | A61B 5/02055 |
| | | | | 600/301 |
| 2014/0322661 | A1* | 10/2014 | Rudman | A61B 5/14507 |
| | | | | 600/309 |
| 2017/0024555 | A1* | 1/2017 | Flitsch | H04L 67/12 |
| 2017/0347956 | A1* | 12/2017 | Zegarelli | A61B 5/682 |
| 2018/0000563 | A1* | 1/2018 | Shanjani | A61B 5/682 |
| 2018/0368961 | A1* | 12/2018 | Shanjani | A61B 5/4547 |
| 2019/0074089 | A1* | 3/2019 | Kochura | G16H 50/20 |
| 2019/0099129 | A1* | 4/2019 | Kopelman | A61B 5/682 |
| 2019/0175104 | A1* | 6/2019 | Malik | A61B 10/0051 |
| 2019/0223751 | A1 | 7/2019 | Weinstein et al. | |
| 2019/0223770 | A1* | 7/2019 | Malik | A61B 5/14546 |
| 2020/0093571 | A1* | 3/2020 | Shanjani | A61B 5/389 |
| 2020/0253551 | A1* | 8/2020 | Fridman | A61C 5/90 |
| 2021/0153991 | A1* | 5/2021 | Chana | A61B 5/4547 |
| 2021/0353387 | A1* | 11/2021 | Velamakanni | A61C 19/063 |
| 2023/0082672 | A1* | 3/2023 | Weinstein | G16H 40/63 |
| 2023/0248312 | A1* | 8/2023 | Fridman | A61B 5/14542 |
| | | | | 600/301 |

FOREIGN PATENT DOCUMENTS

| | | | |
|---|---|---|---|
| JP | 2006309465 A | * | 11/2006 |
| JP | 2015-188558 A | | 11/2015 |
| JP | 2016-010660 A | | 1/2016 |
| JP | 2019057283 A | * | 4/2019 |
| KR | 102038044 B1 | | 10/2019 |
| WO | WO 2012/128121 A1 | | 9/2012 |

OTHER PUBLICATIONS

Extended European Search Report in Europe Application No. 21161636.2, dated Aug. 10, 2021, 7 pages.
Office Action in Japan Application No. 2020-04445, including English translatino, dated Oct. 17, 2023.

* cited by examiner

INTRAORAL SENSING SYSTEM AND INTRAORAL SENSING METHOD

RELATED APPLICATIONS

This application claims priority to Japanese Patent Application No. 2020-044445, filed on Mar. 13, 2020, the entire content of which is incorporated herein by reference.

BACKGROUND OF THE INVENTION

1. Field of the Invention

The present invention relates to an intraoral sensing system and an intraoral sensing method.

2. Description of the Related Art

In the related art, sensors are worn in oral cavities to acquire biological information or sense states of orthodontic appliances or the like worn in oral cavities. For example, with regard to a technique for sensing the states of orthodontic appliances or the like worn in oral cavities, a technique for transmitting an occlusal state in the oral cavity while minimizing an amount of battery to be consumed is known (for example, refer to Japanese Unexamined Patent Application, First Publication No. 2016-10660). In this technique, a mouthpiece is driven using a battery. A sensing unit is composed of a sensor and detects an occlusal state of a subject. A transmission timing setting unit sets a data transmission timing on the basis of the occlusal state detected by the sensing unit. A transmission unit transmits the occlusal state detected by the sensing unit on the basis of the data transmission timing determined using the transmission timing setting unit.

SUMMARY OF THE INVENTION

In the above-described technique, biological information is acquired for a specific purpose through sensing or the like for the purpose of dental treatment.

For this reason, even if the biological information acquired through sensing for the purpose of dental treatment includes daily changes in biological information required for medical treatment, data thereof is never used for medical treatment.

The present invention was made in view of the above problems, and an object thereof is to provide an intraoral sensing system and an intraoral sensing method in which biological information acquired using a sensor module installed in an oral cavity can be used for medical treatment or prevention.

(1) In view of the above object, an intraoral sensing system according to an aspect of the present invention is an intraoral sensing system which is configured to sense a biological information using a sensor module installed in an oral cavity, including: a sensor module installed in an oral cavity of a patient and configured to store data acquired when the biological information is sensed; a storage configured to acquire the data and an identification information of the patient stored by the sensor module, associate the acquired data with the identification information of the patient, and store the association; a terminal apparatus for a dentist configured to analyze the data stored in the storage for each of the identification information of the patient; and a terminal apparatus for a doctor configured to acquire the data associated with a patient who has a developed disease among the data of patients stored in the storage, from the terminal apparatus for a dentist.

(2) In the intraoral sensing system according to the above (1), the sensor module may be installed in any one of an orthodontic appliance, a denture, or an implant.

(3) In the intraoral sensing system according to the above (1) or (2), the biological information may be at least one of a body temperature, a blood flow, oxygen, a heart rate, bacteria, bruxism, and the number of times of chewing and swallowing.

(4) In the intraoral sensing system according to any one of the above (1) to (3), the sensor module may include: a sensor configured to perform sensing in a living body; a battery configured to supply an electric power; a signal processing unit configured to create a digital data on the basis of the results of sensing by the sensor; a memory configured to store digital data created by the signal processing unit; and a wireless transmission/reception unit configured to receive a command used for acquiring data transmitted by an acquisition apparatus and transmit the digital data stored in the memory and the identification information of the patient to the acquisition apparatus on the basis of the received command.

(5) In the intraoral sensing system according to any one of the above (1) to (4), the sensor module may include at least one of a temperature sensor, an acceleration sensor, a gyro sensor, a pressure sensor, a strain sensor, a pulse wave sensor, a pulse oximeter, a heart rate sensor, and a laser sensor.

(6) In the intraoral sensing system according to any one of the above (1) to (5), the sensor module may be installed in any one of an orthodontic appliance, a denture, and an implant; and any one of the orthodontic appliance, the denture, and the implant may be formed to have at least a part including a material through which a light having any wavelength of 400 nm to 1000 nm is able to be transmitted.

(7) In the intraoral sensing system according to any one of the above (1) to (6), the sensor module may transmit an operation confirmation signal; and the intraoral sensing system may include a terminal apparatus configured to receive the operation confirmation signal transmitted by the sensor module.

(8) In the intraoral sensing system according to any one of the above (1) to (7), the terminal apparatus for a dentist may include a processing unit configured to perform either or both of a dental treatment analysis and a medical disease analysis for identification information of the patient on the basis of the data.

(9) In the intraoral sensing system according to the above (8), the processing unit may create a disease information including a patient ID of the patient and information indicating that the patient is suspected of having a disease and destined for terminal apparatus for a doctor when it is determined that the patient is suspected of having a disease; and the terminal apparatus for a dentist may include a communication unit configured to transmit the disease information created by the processing unit to the terminal apparatus for a doctor.

(10) An intraoral sensing method according to an aspect of the present invention is an intraoral sensing method executed using an intraoral sensing system which senses a biological information using a sensor module installed in an oral cavity, including: a step of acquiring, by a storage, a data and an identification information of a patient stored by the sensor module, associating the acquired data with the identification information of the patient, and storing the association; a step of acquiring, by a terminal apparatus for a dentist, the data and the identification information of the patient stored by the sensor module and analyzing the acquired data; a step of creating, by the terminal apparatus for a dentist, a disease information including the identification information of the patient and the information indicating that there is a suspicion of a disease when it is determined that the patient is suspected of having a disease, and transmitting the created disease information to a terminal apparatus for a doctor; a step of creating, by the terminal apparatus for a dentist, a medical clinic information including an information indicating a contact information of a medical clinic in which the terminal apparatus for a doctor which has transmitted the disease information is installed, the identification information of the patient, and a disease name, and transmitting the created medical clinic information to the storage; and a step of storing, by the storage, the medical clinic information transmitted by the terminal apparatus for a dentist.

(11) In the intraoral sensing method according to the above (10), in the step of analysis, the terminal apparatus for a dentist may perform a dental treatment analysis and a medical disease analysis.

(12) In the intraoral sensing method according to the above (10) or (11), the intraoral sensing method may further include a step of acquiring, by the terminal apparatus for a dentist, a data of the patient from the storage on the basis of a sensor information request transmitted by the terminal apparatus for a doctor to request the data of the patient; and a step of creating, by the terminal apparatus for a dentist, a response for sensor information including a data of the patient acquired from the storage, and transmitting the created sensor information response to the terminal apparatus for a doctor.

(13) In the intraoral sensing method according to the above (12), the intraoral sensing method may further include a step of associating, by the terminal apparatus for a dentist, an identification information of the patient corresponding to the data of the patient included in the sensor information response transmitted to the terminal apparatus for a doctor, a disease name, and a medical clinic name with each other, and storing the association in the storage; and a step of acquiring, by the terminal apparatus for a dentist, a name of the patient, the disease name, the medical clinic name, and a treatment information included in the treatment information transmitted by the terminal apparatus for a doctor, associating the acquired identification information of the patient corresponding to the name of the patient, the disease name, the medical clinic name, and the treatment information with each other, and storing the association in the storage.

According to the above aspects of the present invention, it is possible to provide the intraoral sensing system and the intraoral sensing method in which the biological information acquired using the sensor module installed in the oral cavity can be used for medical treatment or prevention.

DETAILED DESCRIPTION OF THE PREFERRED EMBODIMENTS

Figure 1:
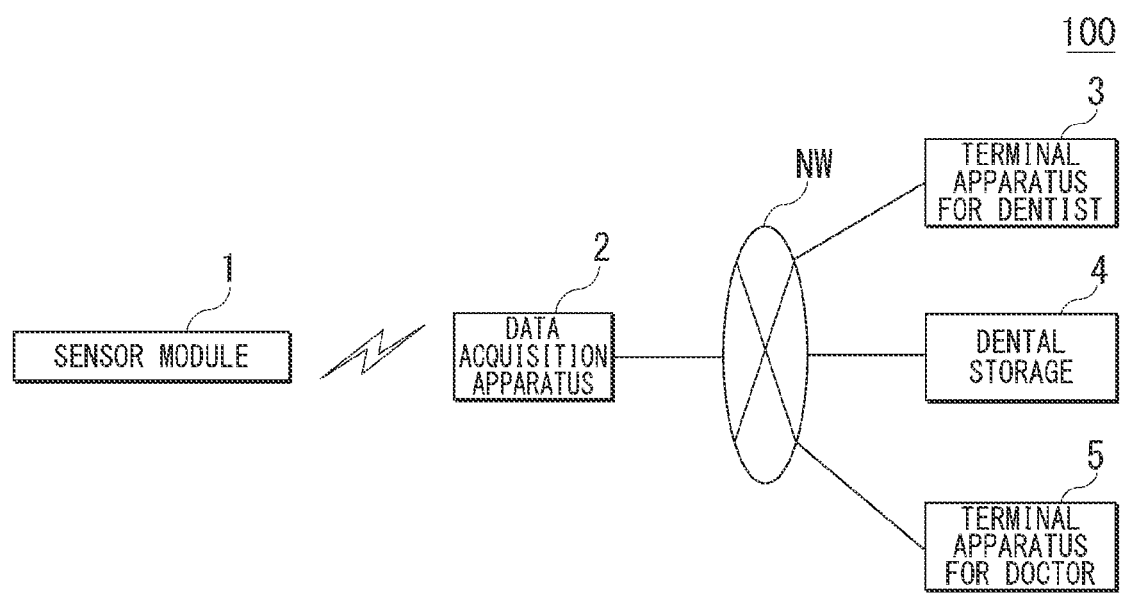
FIG. 1 is a diagram showing an example of an intraoral sensing system in an embodiment of the present invention.

An intraoral sensing system and an intraoral sensing method according to the present embodiment will be described below with reference to the drawings. Embodiments which will be described later are merely examples and embodiments to which the present invention is applied are not limited only to the following embodiments.

Also, the expression "based on XX" described in this specification means the expression "based on at least XX", and includes a case in which the present invention is based on another element in addition to XX. Furthermore, the expression "based on XX" is not limited only to a case in which XX is used directly, and also includes a case in which the calculated and/or processed XX is used. Here, "XX" is an arbitrary element (for example, arbitrary information).

EMBODIMENTS

Embodiments of the present invention will be described below with reference to the drawings. Constituent elements having the same or similar functions are denoted by the same reference numerals and duplicate description regarding these constituent elements may be omitted.

(Intraoral Sensing System)

FIG. 1 is a diagram showing an example of an intraoral sensing system according to an embodiment of the present invention. An intraoral sensing system 100 of the embodiment of the present invention obtains biological information by sensing using a sensor module installed in an oral cavity.

The intraoral sensing system 100 includes a sensor module 1, a data acquisition apparatus 2, a terminal apparatus 3 for a dentist, a dental storage 4, and a terminal apparatus 5 for a doctor.

The sensor module 1 is wirelessly connected to the data acquisition apparatus 2. The data acquisition apparatus 2, the terminal apparatus 3 for a dentist, the dental storage 4, the terminal apparatus 5 for a doctor, and a terminal apparatus 10 communicate with each other over a network NW. The network NW includes, for example, the Internet, wide area networks (WANs), local area networks (LANs), provider apparatuses, wireless base stations, and the like.

The sensor module 1 is attached to an oral cavity of a patient PA and stores the data obtained by sensing biological information in association with date and time information at which the data has been acquired.

The data acquisition apparatus 2 creates a command indicating that sensor information is to be acquired and transmits the created command to the sensor module 1.

The sensor module 1 creates sensor information including stored data, date and time information, and identification information of a patient ID (hereinafter referred to as a "patient ID") when receiving a command indicating that the sensor information transmitted by the data acquisition apparatus 2 is to be acquired, and transmits the created sensor information to the data acquisition apparatus 2.

The data acquisition apparatus 2 receives the sensor information transmitted by the sensor module 1 in response to the transmitted command. The data acquisition apparatus 2 transmits the received sensor information to one or both of the terminal apparatus 3 for a dentist and the dental storage 4.

The dental storage 4 stores the data, the date and time information, and the patient ID included in the sensor information transmitted by the data acquisition apparatus 2 in association with each other.

The terminal apparatus 3 for a dentist acquires the data, the date and time information, and the patient ID included in the sensor information transmitted by the data acquisition apparatus 2. The terminal apparatus 3 for a dentist analyzes the data on the basis of the acquired data and date and time information.

Also, when a user such as a dentist performs an operation for acquiring data, the terminal apparatus 3 for a dentist creates a request for sensor information including information indicating that the patient ID and the data are to be acquired and destined for the dental storage 4. The terminal apparatus 3 for a dentist transmits the created sensor information request to the dental storage 4.

The dental storage 4 acquires data and date and time information stored in association with the patient ID on the basis of the patient ID included in the sensor information request transmitted by the terminal apparatus 3 for a dentist and the information indicating that the data is to be acquired. The dental storage 4 creates a response for sensor information including the acquired data and date and time information. The dental storage 4 transmits the created sensor information response to the terminal apparatus 3 for a dentist.

The terminal apparatus 3 for a dentist receives the sensor information response transmitted by the dental storage 4 in response to the sensor information request transmitted to the dental storage 4. The terminal apparatus 3 for a dentist analyzes the data on the basis of the data and the date and time information included in the sensor information response. That is to say, the terminal apparatus 3 for a dentist analyzes the data stored in the dental storage 4 for each patient ID.

Also, the terminal apparatus 5 for a doctor requests the data stored in association with a patient ID of the patient PA who has developed a disease to the terminal apparatus 3 for a dentist. When a user such as a doctor performs an operation for acquiring data, the terminal apparatus 5 for a doctor creates a request for sensor information including a name of a patient, a disease name, and an information provision period and destined for the terminal apparatus 3 for a dentist. The terminal apparatus 5 for a doctor transmits the created sensor information request to the terminal apparatus 3 for a dentist.

The terminal apparatus 3 for a dentist changes the name of the patient included in the sensor information request to the patient ID when receiving the sensor information request transmitted by the terminal apparatus 5 for a doctor, specifically identifies biological information from the disease name, and creates a request for sensor information including the specifically identified biological information and destined for the dental storage 4. The terminal apparatus 3 for a dentist transfers the created sensor information request to the dental storage 4. The terminal apparatus 3 for a dentist receives the sensor information response transmitted by the dental storage 4 in response to the sensor information request transferred to the dental storage 4. The terminal apparatus 3 for a dentist changes the patient ID included in the received sensor information response to the name of the corresponding patient, specifically identifies a measurement date and time of each piece of digital data on the basis of date and time information regarding starting of sensing and information indicating a measurement time interval, and creates a response for sensor information including the specifically identified measurement date and time and destined for the terminal apparatus 5 for a doctor. The terminal apparatus 3 for a dentist transfers the created sensor information request to the terminal apparatus 5 for a doctor.

The terminal apparatus 5 for a doctor receives the sensor information response transmitted by the terminal apparatus 3 for a dentist in response to the sensor information request transmitted to the terminal apparatus 3 for a dentist. The terminal apparatus 5 for a doctor acquires the name of the patient, the disease name, the digital data, and the information indicating the measurement date and time, included in the sensor information response. A doctor treats a disease on the basis of the acquired disease name, digital data, and information indicating a measurement date and time.

The sensor module 1, the data acquisition apparatus 2, the terminal apparatus 3 for a dentist, the dental storage 4, and the terminal apparatus 5 for a doctor, included in the intraoral sensing system 100 will be described in detail below.

Figure 2:
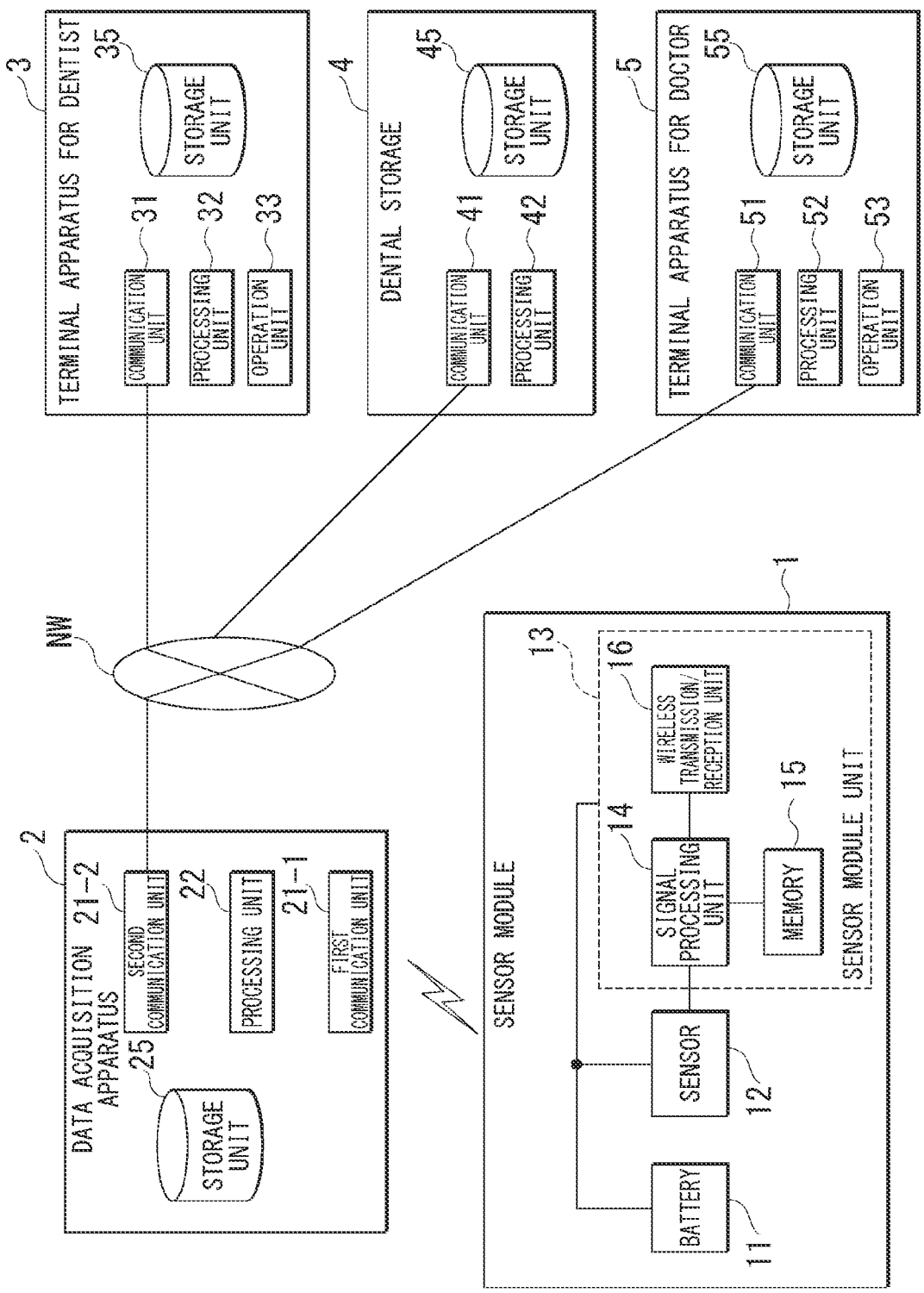
FIG. 2 is a block diagram showing an example of a sensor module, a data acquisition apparatus, a terminal apparatus for a dentist, a dental storage, and a terminal apparatus for a doctor included in the intraoral sensing system of the present embodiment.

FIG. 2 is a block diagram showing an example of the sensor module, the data acquisition apparatus, the terminal apparatus for a dentist, the dental storage, and the terminal apparatus for a doctor included in the intraoral sensing system in this embodiment.

(Sensor Module 1)

The sensor module 1 includes a battery 11, a sensor 12, and a sensor module unit 13. Circuit blocks such as the battery 11, the sensor 12, and the sensor module unit 13 are installed above a thin circuit board or a flexible board. An example of the sensor module unit 13 is implemented using a chip including a signal processing unit 14, a memory 15, and a wireless transmission/reception unit 16. The sensor module 1 can be attached to orthodontic appliances or dentures or embedded in an implant.

Figure 3:
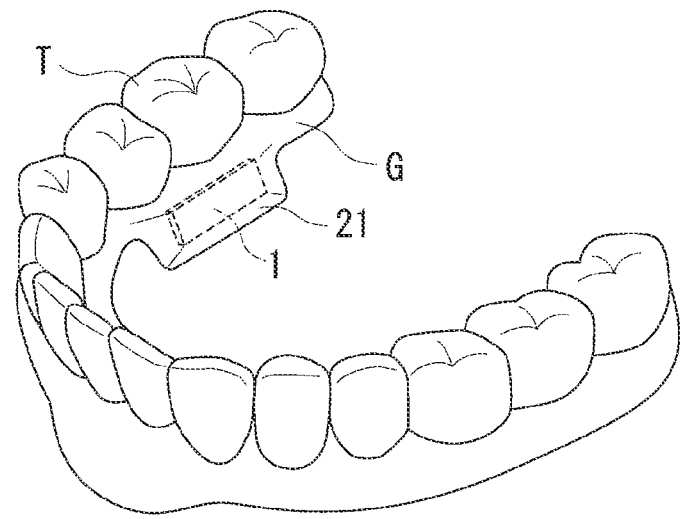
FIG. 3 is a diagram showing a first example of an external form of a sensor module of an intraoral biological monitoring system according to the present embodiment.

FIG. 3 is a diagram showing a first example of an external form of a sensor module of an intraoral biological monitoring system of the present embodiment.

Figure 4:
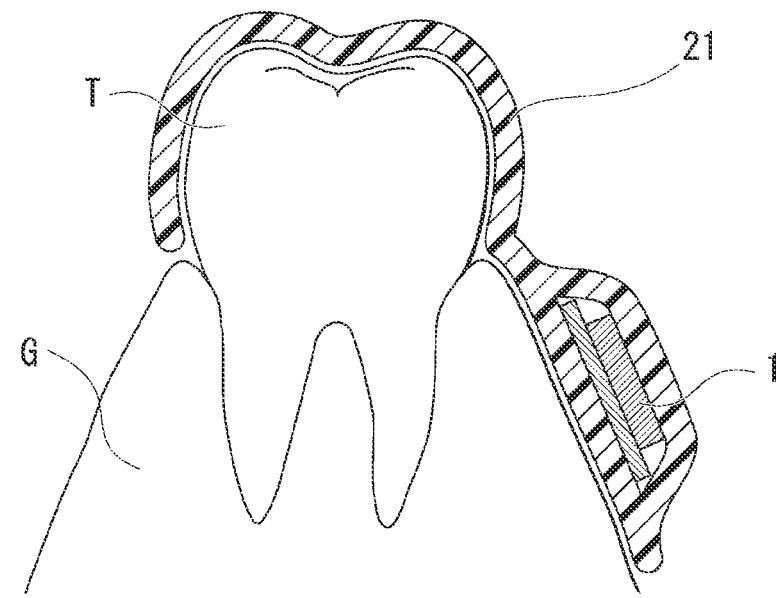
FIG. 4 is a diagram showing a first example of a cross section of a portion of the intraoral biological monitoring system according to the present embodiment, where the sensor module is attached.

FIG. 4 is a diagram showing a first example of a cross section of a portion of the intraoral biological monitoring system according to the present embodiment, where the sensor module is attached.

As shown in FIGS. 3 and 4, the sensor module 1 is held by a mouthpiece 21. An example of the mouthpiece 21 is manufactured such that at least a part of which is made of a material through which light is transmitted. As an example of the mouthpiece 21, the mouthpiece 21 is installed in a crown T while covering at least one of the crown T and a gum G of a test object (the patient PA). Furthermore, as an example of the mouthpiece 21, the mouthpiece 21 covers at least a part of the gum G of the test object. In addition, as an example of the mouthpiece 21, the mouthpiece 21 covers at least a part of the sensor module 1. To be specific, the mouthpiece 21 seals at least a part of the sensor module 1. In the example shown in FIG. 3, the sensor module 1 is installed on the inner side of the teeth.

Figure 5:
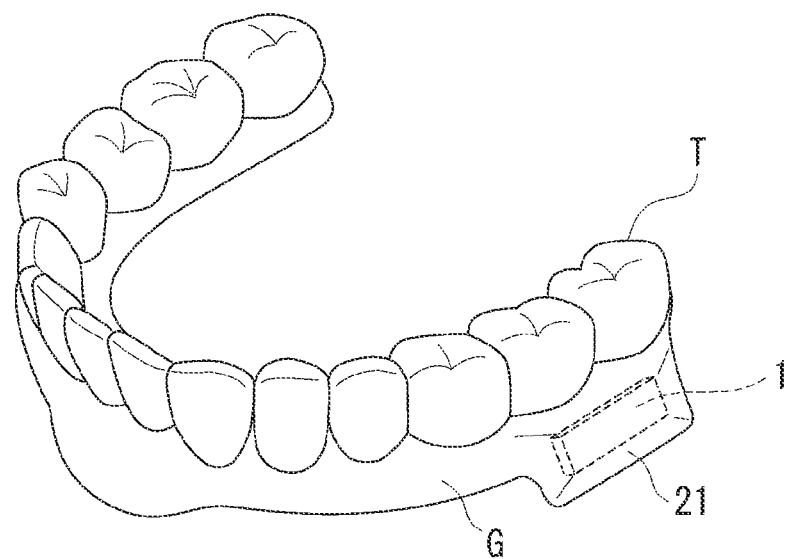
FIG. 5 is a diagram showing a second example of the external form of the sensor module of the intraoral biological monitoring system according to the present embodiment.

FIG. 5 is a diagram showing a second example of the external form of the sensor module of the intraoral biological monitoring system in this embodiment. In the example shown in FIG. 5, the sensor module 1 is installed on the outer side of the teeth.

In a case where the sensor module 1 is installed in an orthodontic appliance as shown in FIGS. 3 to 5, the orthodontic appliance is constituted to include any of a polyethylene-based material, a polyurethane-based material, and a thermoplastic polymer compound of an acrylic-based resin. The orthodontic appliance is formed into a teeth shape and a gum shape by using molding techniques such as embossing and 3D printers.

A recess is formed in a part of the orthodontic appliance and the sensor module 1 is installed in the formed recess. A place having the sensor module 1 installed therein may be either a portion corresponding to a side wall of a crown portion or a portion corresponding to a gum. When the engagement between the upper teeth and the lower teeth is considered, as shown in FIG. 4, it is desirable that the sensor module 1 be installed in the portion corresponding to the gum.

Also, when at least one of pulse wave sensors configured to measure pulse waves using light, pulse oximeters configured to measure an oxygen concentration in blood using light, heart rate sensors configured to measure a heart rate using light, and laser sensors configured to measure a blood flow using laser light is installed in the sensor module 1, the sensor module 1 acquires information from the blood vessels in the gum portion. Thus, it is desirable to install the sensor module 1 in the gum portion.

Also, when the sensor module 1 has a sensor in which light or a laser is utilized installed therein, the transmission of light is essential. Thus, at least a part of the orthodontic appliance needs to be made of a material through which any wavelength of light of 400 nm to 1000 nm can be transmitted.

Figure 6:
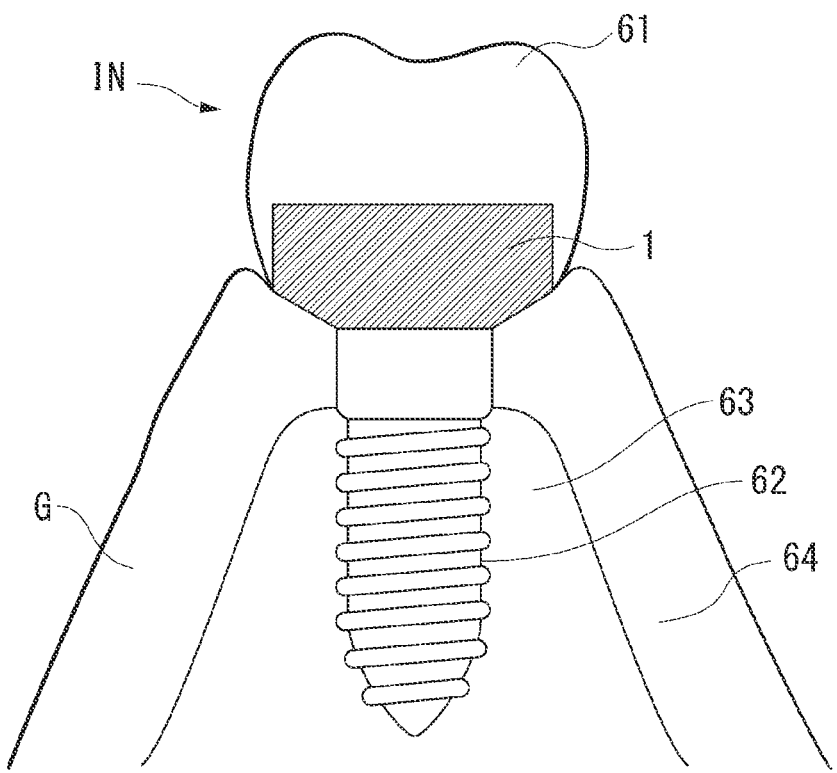
FIG. 6 is a diagram showing a second example of the cross section of the portion having the sensor module of the intraoral biological monitoring system according to the present embodiment, where the sensor module is attached.

FIG. 6 is a diagram showing a second example of the cross section of the portion to which the sensor module of the intraoral biological monitoring system in this embodiment is attached. In the example shown in FIG. 6, the sensor module 1 is embedded in an implant IN. The implant IN includes an implant body 63. The implant body 63 includes a screw part 62 to be embedded inside a bone 64 for implantation and a head part 61 connected to the screw part 62.

As shown in FIG. 6, when the sensor module 1 is installed in the implant IN, the sensor module 1 is installed in the head part 61 such as an implant denture. When the sensor module 1 is installed in the head part 61 and at least one of a pulse wave sensor configured to measure pulse waves using light, a pulse oximeter configured to measure an oxygen concentration in blood using light, a heart rate sensor configured to measure a heart rate using light, and a laser sensor configured to measure a blood flow using laser light is installed in the sensor module 1, it is desirable to install the sensor module 1 in the portion corresponding to the gum to acquire information from the blood vessels of the gum.

Also, when the sensor module 1 has a sensor in which light or a laser is utilized installed therein, the transmission of light is essential. Thus, at least a part of the head part 61 needs to be made of a material through which any wavelength of light of 400 nm to 1000 nm can be transmitted. Referring to FIG. 2 again, the explanation will be continued.

An example of the battery 11 includes primary batteries or secondary batteries. The battery 11 supplies electric power to the sensor 12 and the sensor module unit 13.

The sensor 12 includes at least one of temperature sensors, acceleration sensors, gyro sensors, pressure sensors, strain sensors, pulse wave sensors, pulse oximeters, heart rate sensors, and laser sensors, and acquires sensing data through sensing. Here, the pulse wave sensor measures pulse waves using light, the pulse oximeter measures an oxygen concentration in blood using light, the heart rate sensor measures a heart rate using light, and the laser sensor measures a blood flow using laser light.

Also, as described above, the sensor module 1 may be constituted to include at least one of a pulse wave sensor configured to measure pulse waves using light, a pulse oximeter configured to measure an oxygen concentration in blood using light, a heart rate sensor configured to measure a heart rate using light, and a laser sensor configured to measure a blood flow using laser light. Furthermore, the sensor module 1 may be constituted to include a sensor in which light or a laser is utilized. The sensor 12 outputs the acquired sensing data to the sensor module unit 13. Here, the sensing data (sensor data) is output value of the sensor 12 installed in the sensor module 1. For example, when a temperature sensor and an acceleration sensor are installed in the sensor module 1, the temperature sensor and the acceleration sensor output a temperature sensor value and an acceleration sensor value (x,y,z) for each of measurement intervals.

The wireless transmission/reception unit 16 communicates with the data acquisition apparatus 2. An example of a wireless communication method used for communication between the wireless transmission/reception unit 16 and the data acquisition apparatus 2 includes Bluetooth low energy (BLE). Here, wireless communication may be performed between the wireless transmission/reception unit 16 and the data acquisition apparatus 2 through a communication method other than BLE.

To be specific, the wireless transmission/reception unit 16 receives initial setting information transmitted by the data acquisition apparatus 2. The initial setting information includes date and time information regarding starting of sensing by the sensor module 1, information indicating a measurement time interval, and a patient ID. Here, the date and time information may include information indicating the year and month.

Also, the wireless transmission/reception unit 16 receives the command transmitted by the data acquisition apparatus 2. The wireless transmission/reception unit 16 acquires the sensor information output by the signal processing unit 14, and transmits the acquired sensor information to the data acquisition apparatus 2 outside the oral cavity.

The signal processing unit 14 is constituted to include a microcomputer and an analog to digital converting circuit (ADC: analog to digital converter). The signal processing unit 14 acquires the initial setting information received by the wireless transmission/reception unit 16, and obtains the date and time information regarding the starting of the sensing, the information indicating the measurement time interval, and the patient ID, each included in the acquired initial setting information. The signal processing unit 14 stores the acquired date and time information regarding the starting of the sensing, information indicating the measurement time interval, and the patient ID in the memory 15. Furthermore, the signal processing unit 14 sets the acquired information indicating a measurement time interval in the sensor 12.

The signal processing unit 14 acquires the sensing data output by the sensor 12 and converts the acquired sensing data into digital data. The signal processing unit 14 associates the digital data obtained through the conversion of the sensing data with a measurement index, and stores the association in the memory 15. Here, the measurement index is identification information of the digital data. The measurement index and the sensor data are stored for each measurement interval. An example of the measurement index is a numerical value which is uniquely determined and assigned in the order of measurement.

The signal processing unit 14 acquires the command received by the wireless transmission/reception unit 16 and interprets the acquired command. The signal processing unit 14 controls the memory 15 and the wireless transmission/reception unit 16 on the basis of the result of interpreting the command. To be specific, when the command received by the wireless transmission/reception unit 16 is to acquire the sensor information, the signal processing unit 14 creates sensor information destined for the data acquisition apparatus 2, which includes information obtained by associating date and time information regarding the starting of the sensing, information indicating the measurement time interval, a patient ID, an ID of the sensor module 1 (an ID of a sensor 12), a measurement index, and digital data, each stored in the memory 15, with each other. Here, the ID of the sensor module 1 is identification information of the sensor module 1. The signal processing unit 14 outputs the created sensor information to the wireless transmission/reception unit 16.

(Data Acquisition Apparatus 2)

The data acquisition apparatus 2 is implemented using an apparatus such as a personal computer, a server, a smartphone, a tablet computer, or an industrial computer. The data acquisition apparatus 2 includes, for example, a first communication unit 21-1, a second communication unit 21-2, a processing unit 22, and a storage unit 25.

The first communication unit 21-1 is implemented using a communication module. The first communication unit 21-1 communicates with an external communication apparatus. The first communication unit 21-1 may communicate through a communication method such as BLE. The first communication unit 21-1 holds communication information required for communicating with the sensor module 1. The first communication unit 21-1 transmits the initial setting information output by the processing unit 22 to the sensor module 1. The first communication unit 21-1 transmits the command output by the processing unit 22 to the sensor module 1. The first communication unit 21-1 receives the sensor information transmitted by the sensor module 1 in response to the transmitted command.

The second communication unit 21-2 is implemented using a communication module. The second communication unit 21-2 communicates with an external communication apparatus over the network NW. For example, the second communication unit 21-2 may communicate through a communication method such as a wired LAN. The second communication unit 21-2 holds communication information required for communicating with the terminal apparatus 3 for a dentist and the dental storage 4 over the network NW. The second communication unit 21-2 receives a sensor information acquisition request transmitted by the terminal apparatus 3 for a dentist. The second communication unit 21-2 transmits the sensor information output by the processing unit 22 to the terminal apparatus 3 for a dentist. The second communication unit 21-2 transmits the sensor information output by the processing unit 22 to the dental storage 4.

The storage unit 25 is implemented using a hard disk drive (HDD), a flash memory, a random access memory (RAM), a read only memory (ROM), or the like.

The processing unit 22 is realized using, for example, a computer program (software) stored in the storage unit 25 and executed by a hardware processor such as a CPU. Furthermore, some or all of these functional units may be implemented using hardware (circuit units; including circuitries) such as large scale integrations (LSIs), application specific integrated circuits (ASICs), field-programmable gate arrays (FPGAs), and graphics processing units (GPUs) or be realized through the cooperation of software and hardware. The computer program may be stored in a storage apparatus such as hard disk drives (HDDs) and flash memories in advance, or be stored in an attachable/detachable storage medium such as DVDs and CD-ROMs, and installed when the storage medium is installed in a drive apparatus.

The processing unit 22 creates initial setting information including date and time information regarding starting of sensing, information indicating a measurement time interval, and a patient ID. The processing unit 22 creates initial setting information when the sensor module 1 has started up and it is detected that the sensor module 1 has started up. The processing unit 22 outputs the created initial setting information to the first communication unit 21-1. The processing unit 22 acquires the sensor information acquisition request received by the second communication unit 21-2. The processing unit 22 creates a command for acquiring sensor information on the basis of the acquired sensor information acquisition request. The processing unit 22 outputs the created command to the first communication unit 21-1. The processing unit 22 acquires the sensor information received by the first communication unit 21-1. The processing unit 22 outputs the acquired sensor information to the second communication unit 21-2.

(Terminal Apparatus 3 for a Dentist)

The terminal apparatus 3 for a dentist is implemented using an apparatus such as a personal computer, a server, a smartphone, a tablet computer, or an industrial computer. The terminal apparatus 3 for a dentist is installed in a clinic such as a dental clinic in which teeth are examined and treated. The terminal apparatus 3 for a dentist includes, for example, a communication unit 31, a processing unit 32, an operation unit 33, and a storage unit 35.

The communication unit 31 is implemented using a communication module. The communication unit 31 communicates with an external communication apparatus over the network NW. The communication unit 31 may communicate through, for example, a communication method such as a wired LAN. The communication unit 31 holds communication information required for communicating with the data acquisition apparatus 2, the dental storage 4, and the terminal apparatus 5 for a doctor over the network NW.

To be specific, the communication unit 31 transmits the sensor information acquisition request output by the processing unit 32 to the data acquisition apparatus 2, and receives the sensor information transmitted by the data acquisition apparatus 2 in response to the transmitted sensor information acquisition request. The communication unit 31 transmits the sensor information request output by the processing unit 32 to the dental storage 4, and receives the sensor information response transmitted by the dental storage 4 in response to the transmitted sensor information request.

The communication unit 31 receives the sensor information request transmitted by the terminal apparatus 5 for a doctor, and transmits the sensor information request output by the processing unit 32 to the dental storage 4 in response to the received sensor information request. The communication unit 31 receives the sensor information response transmitted by the dental storage 4, and transmits the sensor information response output by the processing unit 32 to the terminal apparatus 5 for a doctor in response to the received sensor information response.

The operation unit 33 includes an input apparatus and receives an operation of a dentist. The input apparatus includes a device configured to input character information such as a keyboard, a pointing device such as a mouse and a touch panel, a button, a dial, a joystick, a touch sensor, a touch pad, and the like. A dentist inputs one or both of information used for requesting the acquisition of sensor information and a patient ID by operating the operation unit 33.

The storage unit 35 is implemented using an HDD, a flash memory, a RAM, a ROM, or the like.

The processing unit 32 is realized using, for example, a computer program (software) stored in the storage unit 35 and executed by a hardware processor such as a CPU. Furthermore, some or all of these functional units may be implemented using hardware (circuit units; including circuitries) such as an LSI, an ASIC, an FPGA, and a GPU or realized through the cooperation of software and hardware. The computer program may be stored in a storage apparatus such as an HDD or a flash memory in advance, or be stored in an attachable/detachable storage medium such as a DVD or a CD-ROM, and installed when the storage medium is installed in a drive apparatus.

The processing unit 32 creates sensor information acquisition request on the basis of the information used for requesting the acquisition of sensor information output by the operation unit 33 when a user such as a dentist operates the operation unit 33, and outputs the created sensor information acquisition request to the communication unit 31. The processing unit 32 acquires the sensor information transmitted by the data acquisition apparatus 2 from the communication unit 31 in response to the sensor information acquisition request. The processing unit 32 acquires date and time information regarding starting of sensing, information indicating a measurement time interval, a patient ID, the ID of the sensor module 1, a measurement index, and digital data included in the acquired sensor information. The processing unit 32 extracts digital data required for the dental treatment of the patient PA from the acquired digital data. The processing unit 32 performs analysis required for the dental treatment on the basis of the extracted digital data, date and time information regarding starting of sensing associated with the extracted digital data, and information indicating a measurement time interval.

Also, the processing unit 32 creates a request for sensor information including a patient ID in which sensor information is required and information used for requesting sensor information and destined for the dental storage 4 on the basis of the information used for requesting the acquisition of sensor information output by the operation unit 33 and the patient ID, when a user such as a dentist operates the operation unit 33. The processing unit 32 outputs the created sensor information request to the communication unit 31. The processing unit 32 acquires the sensor information response transmitted by the dental storage 4 from the communication unit 31 in response to the sensor information request. The processing unit 32 acquires date and time information regarding starting of sensing included in the acquired sensor information response, information indicating a measurement time interval, a patient ID, the ID of the sensor module 1, a measurement index, and digital data. The processing unit 32 extracts digital data required for the dental treatment of the patient PA from the acquired digital data. The processing unit 32 performs analysis required for the dental treatment on the basis of the extracted digital data, date and time information regarding starting of sensing associated with the extracted digital data, and information indicating a measurement time interval.

Also, the processing unit 32 acquires the sensor information request transmitted by the terminal apparatus 5 for a doctor from the communication unit 31, changes a name of a patient included in the acquired sensor information request to a corresponding patient ID, specifically identifies biological information from a disease name, and outputs a request for sensor information including the specifically identified biological information and destined for the dental storage 4, to the communication unit 31. For example, the terminal apparatus 3 for a dentist has a database constructed so that a disease name and sensor data relating to the disease are associated with each other. The processing unit 32 acquires the disease name included in the sensor information request and acquires the sensor data associated with the acquired disease name.

To be specific, the processing unit 32 can acquire a disease name A from the sensor information request and specifically identify temperature sensor data associated with the acquired disease name A. The processing unit 32 can acquire a disease name B from the sensor information request and specifically identify temperature sensor data and acceleration sensor data associated with the acquired disease name B. With such a constitution, it is possible to prevent the information from being provided at the discretion of each dentist. That is to say, the problem of different data provided by dentists is eliminated. The processing unit 32 acquires the sensor information response transmitted by the dental storage 4 from the communication unit 31 in response to the sensor information request. The processing unit 32 changes the patient ID included in the acquired sensor information response to a name of a corresponding patient, specifically identifies measurement date and time of each digital data on the basis of the date and time information regarding starting of sensing and information indicating a measurement time interval, and outputs a response for sensor information including the specifically identified measurement date and time and destined for the terminal apparatus 5 for a doctor, to the communication unit 31.

(Dental Storage 4)

The dental storage 4 is implemented using an apparatus such as a personal computer, a server, or an industrial computer. An example of the dental storage 4 is installed in a clinic such as a dental clinic in which teeth are examined and treated. Furthermore, the dental storage 4 may be realized in a cloud. The dental storage 4 includes, for example, a communication unit 41, a processing unit 42, and a storage unit 45.

The communication unit 41 is implemented using a communication module. The communication unit 41 communicates with an external communication apparatus over the network NW. The communication unit 41 may communicate through, for example, a communication method such as a wired LAN. The communication unit 41 holds communication information required for communicating with the data acquisition apparatus 2 and the dental storage 4 over the network NW. To be specific, the communication unit 41 receives the sensor information transmitted by the data acquisition apparatus 2. The communication unit 41 receives the sensor information request transmitted by the terminal apparatus 3 for a dentist, and transmits the sensor information response output by the processing unit 42 to the terminal apparatus 3 for a dentist in response to the received sensor information request.

The storage unit 45 is implemented using an HDD, a flash memory, a RAM, a ROM, or the like.

The processing unit 42 is realized using, for example, a computer program (software) stored in the storage unit 45 and executed by a hardware processor such as a CPU. Furthermore, some or all of these functional units may be implemented using hardware (circuit units; including circuitries) such as LSIs, ASICs, FPGAs, and GPUs or be realized through the cooperation of software and hardware. The computer program may be stored in a storage apparatus such as HDDs and flash memories in advance, or be stored in an attachable/detachable storage medium such as DVDs and CD-ROMs, and installed when the storage medium is installed in a drive apparatus.

The processing unit 42 acquires the sensor information received by the communication unit 41, and obtains date and time information regarding starting of sensing, information indicating a measurement time interval, a patient ID, the ID of the sensor module 1, a measurement index, and digital data each included in the acquired sensor information. The processing unit 42 associates the acquired date and time information regarding starting of sensing, the information indicating a measurement time interval, the patient ID, the ID of the sensor module 1, the measurement index, and the digital data with each other and stores the association in the storage unit 45.

Also, the processing unit 42 acquires the sensor information request received by the communication unit 41, and obtains a patient ID in which sensor information is required and information used for requesting sensor information each included in the acquired sensor information request. The processing unit 42 acquires date and time information regarding starting of sensing, information indicating a measurement time interval, the ID of the sensor module 1, a measurement index, and digital data, each stored in association with the acquired patient ID. The dental storage 4 creates a response for sensor information destined for the terminal apparatus 3 for a dentist, which includes the patient ID and the acquired date and time information regarding starting of sensing, information indicating a measurement time interval, ID of sensor module 1, measurement index, and digital data. The dental storage 4 transmits the created sensor information response to the terminal apparatus 3 for a dentist.

(Terminal Apparatus 5 for a Doctor)

The terminal apparatus 5 for a doctor is implemented using an apparatus such as a personal computer, a server, a smartphone, a tablet computer, or an industrial computer. The terminal apparatus 5 for a doctor is installed in a clinic in which a disease is treated such as a medical clinic. The terminal apparatus 5 for a doctor includes, for example, a communication unit 51, a processing unit 52, an operation unit 53, and a storage unit 55.

The communication unit 51 is implemented using a communication module. The communication unit 51 communicates with an external communication apparatus over the network NW. The communication unit 51 may communicate through, for example, a communication method such as a wired LAN. The communication unit 51 holds communication information required for communicating with the terminal apparatus 3 for a dentist over the network NW. To be specific, the communication unit 51 transmits the sensor information request output by the processing unit 52 to the terminal apparatus 3 for a dentist, and receives the sensor information response transmitted by the terminal apparatus 3 for a dentist.

The operation unit 53 includes an input apparatus and receives an operation of a user such as a doctor. The input apparatus includes a device configured to input character information such as a keyboard, a pointing device such as a mouse and a touch panel, a button, a dial, a joystick, a touch sensor, a touch pad, and the like. A doctor inputs information used for requesting the acquisition of sensor information and a patient ID by operating the operation unit 53.

The storage unit 55 is implemented using an HDD, a flash memory, a RAM, a ROM, or the like.

The processing unit 52 is realized using, for example, a computer program (software) stored in the storage unit 55 and executed by a hardware processor such as a CPU. Furthermore, some or all of these functional units may be implemented using hardware (circuit units; including circuitries) such as an LSI, an ASIC, an FPGA, and a GPU or be realized through the cooperation of software and hardware. The computer program may be stored in a storage apparatus such as HDDs and flash memories in advance, or be stored in an attachable/detachable storage medium such as DVDs and CD-ROMs, and installed when the storage medium is installed in a drive apparatus.

The processing unit 52 acquires a disease name and a name of a patient output by the operation unit 53 when a user such as a doctor operates the operation unit 53. The processing unit 52 creates a request for sensor information destined for the terminal apparatus 3 for a dentist, which includes a name of a patient in which the acquired sensor information is required and a disease name. The processing unit 52 outputs the created sensor information request to the communication unit 51. The processing unit 52 acquires the sensor information response transmitted by the terminal apparatus 3 for a dentist from the communication unit 51 in response to the sensor information request. The processing unit 52 acquires a name of a patient, a disease name, digital data, and information indicating a measurement date and time included in the acquired sensor information response. The processing unit 52 performs a treatment for a disease on the basis of the acquired disease name, the digital data, and the information indicating a measurement date and time.

An operation of the intraoral sensing system 100 will be described below.

(Operation of Intraoral Sensing System 100)

Figure 7:
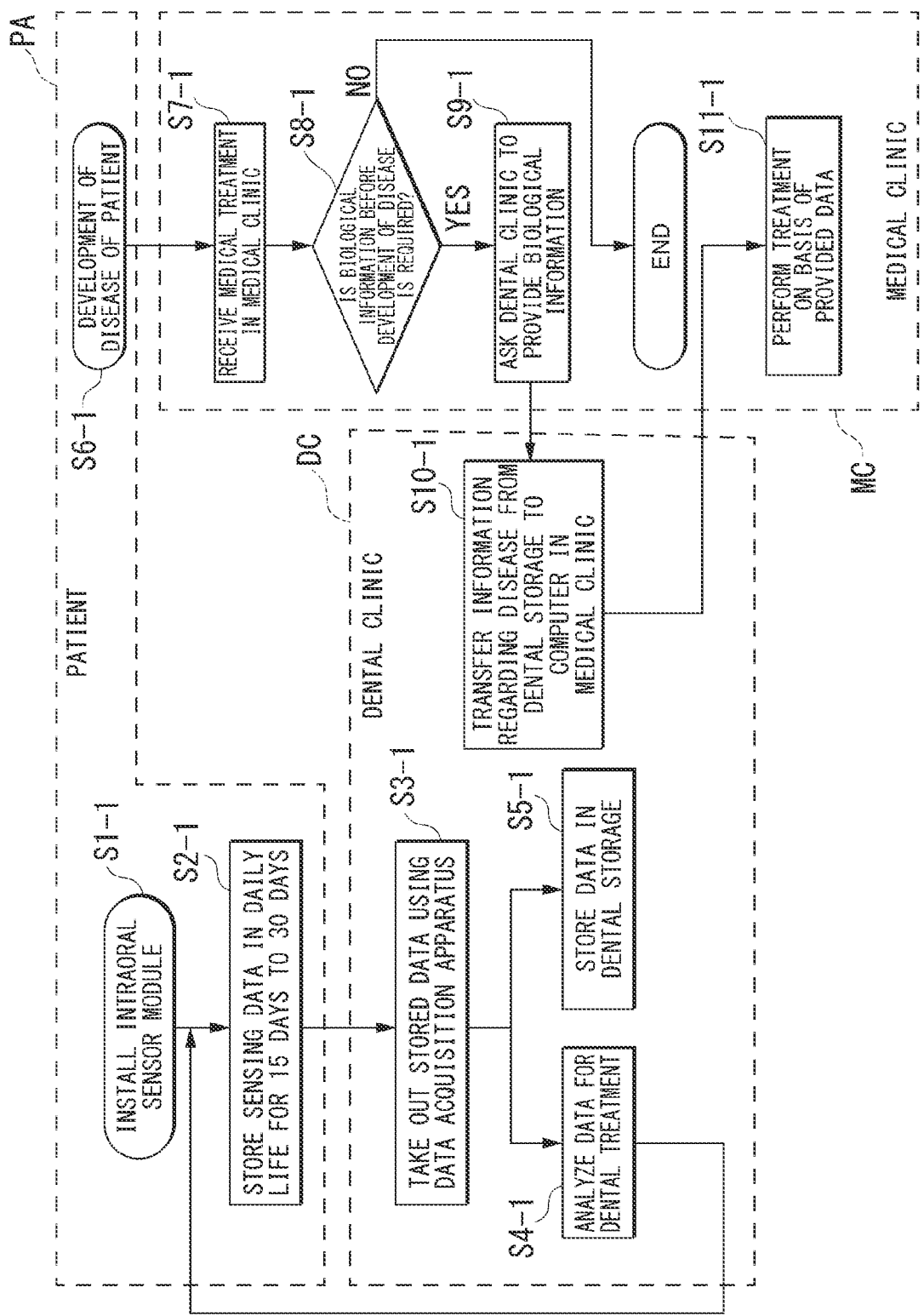
FIG. 7 is a flowchart showing a first example of an operation of the intraoral sensing system according to the present embodiment.

FIG. 7 is a flowchart showing a first example of an operation of the intraoral sensing system in this embodiment.

(Step S1-1) The patient PA wears the sensor module 1.

(Step S2-1) The data acquisition apparatus 2 creates initial setting information including date and time information regarding starting of sensing, information indicating a measurement time interval, and a patient ID. The data acquisition apparatus 2 transmits the created initial setting information to the sensor module 1.

The sensor module 1 receives the initial setting information transmitted by the data acquisition apparatus 2. The sensor module 1 acquires date and time information regarding starting of sensing, information indicating a measurement time interval, and a patient ID included in the received initial setting information. The signal processing unit 14 stores the acquired date and time information regarding starting of sensing, information indicating a measurement time interval, and patient ID in the memory 15. Furthermore, the signal processing unit 14 sets information indicating the acquired measurement time interval in the sensor 12.

The sensor 12 acquires sensing data at a cycle corresponding to the measurement time interval. The sensor 12 outputs the acquired sensing data to the sensor module unit 13. The signal processing unit 14 acquires the sensing data output by the sensor 12 and converts the acquired sensing data into digital data. The signal processing unit 14 associates the digital data obtained by converting the sensing data with the measurement index, and stores the association in the memory 15. The sensor module 1 associates the digital data in daily life with the measurement index for a prescribed period such as 15 days to 30 days, and stores the association in the memory 15.

(Step S3-1) After a prescribed period has elapsed, the patient PA visits a dental clinic. A dentist takes out the sensor module 1.

The terminal apparatus 3 for a dentist creates sensor information acquisition request on the basis of an operation of a user such as a dentist, and transmits the created sensor information acquisition request to the data acquisition apparatus 2.

The data acquisition apparatus 2 receives the sensor information acquisition request transmitted by the terminal apparatus 3 for a dentist, creates a command indicating the acquisition of sensor information on the basis of the received sensor information acquisition request, and transmits the created command to the sensor module 1.

In the sensor module 1, the wireless transmission/reception unit 16 receives the command transmitted by the data acquisition apparatus 2. The signal processing unit 14 acquires the command received by the wireless transmission/reception unit 16; and if the acquired command indicates the acquisition of sensor information, then the signal processing unit 14 creates sensor information destined for the data acquisition apparatus 2, which includes information obtained by associating the date and time information regarding starting of sensing, the information indicating a measurement time interval, the patient ID, the ID of the sensor module 1, the measurement index, and the digital data, each stored in the memory 15, with each other. The signal processing unit 14 outputs the created sensor information to the wireless transmission/reception unit 16. The wireless transmission/reception unit 16 acquires the sensor information output by the signal processing unit 14, and transmits the acquired sensor information to the data acquisition apparatus 2. The data acquisition apparatus 2 receives the sensor information transmitted by the sensor module 1.

(Step S4-1) The terminal apparatus 3 for a dentist creates sensor information request on the basis of an operation of a user such as a dentist, and transmits the created sensor information request to the data acquisition apparatus 2.

The data acquisition apparatus 2 creates sensor information response on the basis of the sensor information request transmitted by the terminal apparatus 3 for a dentist. The data acquisition apparatus 2 transmits the created sensor information response to the terminal apparatus 3 for a dentist.

The terminal apparatus 3 for a dentist receives the sensor information response transmitted by the data acquisition apparatus 2 in response to the sensor information request. The terminal apparatus 3 for a dentist acquires date and time information regarding starting of sensing, information indicating a measurement time interval, a patient ID, the ID of the sensor module 1, a measurement index, and digital data, each included in the received sensor information response. The terminal apparatus 3 for a dentist extracts digital data required for the dental treatment of the patient PA from the acquired digital data. The terminal apparatus 3 for a dentist performs analysis required for the dental treatment on the basis of the extracted digital data, the date and time information regarding starting of sensing associated with the extracted digital data, and information indicating a measurement time interval. For example, the terminal apparatus 3 for a dentist calculates a time at which the patient PA wears an orthodontic appliance from temperature information or calculates the number of chewing of the patient PA from acceleration information. After that, the process proceeds to the process of Step S1-1.

From the results of analysis using the terminal apparatus 3 for a dentist, a dentist formulates a treatment plan for a prescribed period such as the next 15 days to 30 days. The patient PA wears the sensor module 1 in the oral cavity again and acquires digital data in daily life for a prescribed period such as for 15 days to 30 days. After that, this is repeatedly performed.

(Step S5-1) The data acquisition apparatus 2 stores the received sensor information in the dental storage 4.

(Step S6-1) The patient PA develops a disease.

(Step S7-1) The patient PA has a medical checkup in a medical clinic MC.

(Step S8-1) A doctor determines whether biological information before the development of the disease of the patient PA is required. When it is determined that the biological information is not required, the process ends.

(Step S9-1) When it is determined that the biological information before the development of the disease of the patient PA is required, the doctor asks a dental clinic to provide the biological information. To be specific, the terminal apparatus 5 for a doctor creates a request for sensor information including a name of a patient and a disease name and destined for the terminal apparatus 3 for a dentist on the basis of an operation of a user such as a doctor, and transmits the created sensor information request to the terminal apparatus 3 for a dentist.

(Step S10-1) The terminal apparatus 3 for a dentist receives the sensor information request transmitted by the terminal apparatus 5 for a doctor, changes a name of a patient included in the received sensor information request into a corresponding patient ID, specifically identifies biological information from a disease name, and transmits a request for sensor information including the specifically identified biological information and destined for the dental storage 4, to the dental storage 4.

The dental storage 4 receives the sensor information request transferred by the terminal apparatus 3 for a dentist, and acquires the date and time information regarding starting of sensing, the information indicating a measurement time interval, and the digital data stored in association with the patient ID, on the basis of the patient ID and the biological information included in the received sensor information request. The dental storage 4 creates a response for sensor information destined for the terminal apparatus 3 for a dentist, which includes the patient ID, the acquired date and time information regarding starting of sensing, information indicating a measurement time interval, and digital data. The dental storage 4 transmits the created sensor information response to the terminal apparatus 3 for a dentist.

The terminal apparatus 3 for a dentist receives the sensor information response transmitted by the dental storage 4. The terminal apparatus 3 for a dentist changes the patient ID included in the received sensor information response to a name of a corresponding patient, specifically identifies measurement date and time of each digital data on the basis of the date and time information regarding starting of sensing and the information indicating a measurement time interval, and transfers a response for sensor information destined for the terminal apparatus 5 for a doctor, which includes the specifically identified measurement date and time, to the terminal apparatus 5 for a doctor.

(Step S11-1) The terminal apparatus 5 for a doctor receives the sensor information response transferred by the terminal apparatus 3 for a dentist. The terminal apparatus 5 for a doctor acquires a name of a patient, a disease name, digital data, and information indicating a measurement date and time included in the received sensor information response. A doctor treats a disease on the basis of the acquired disease name, digital data, and information indicating a measurement date and time.

As an example, a case in which the sensor module 1 is installed in an orthodontic appliance will be described.

When a treatment starts, a dentist first measures an initial position of the tooth of the patient PA and calculates a final position of the tooth using an orthodontic design system. In the orthodontic design system, a treatment plan is calculated from the initial position of the tooth and the final position of the tooth to prepare first orthodontic appliance preparation data. Here, the first orthodontic appliance preparation data is not necessarily to be one data and a plurality of orthodontic appliance preparation data may be created. The created orthodontic appliance preparation data is transmitted to the orthodontic appliance preparation system, and an orthodontic appliance is prepared using the orthodontic appliance preparation system.

The patient PA wears the prepared orthodontic appliance. When the patient PA wears the orthodontic appliance, the treatment is started. The patient PA wears the orthodontic appliance in accordance with a prescribed period such as a wearing time instructed by a dentist. Here, when the patient PA is a child or the like, the wearing time may be a prescribed period or less such as a wearing time instructed by a dentist in some cases.

The patient PA regularly visits a dentist and asks confirmation of the condition of an alignment of teeth. The dentist connects the sensor module 1 installed in the orthodontic appliance submitted from the patient PA to the data acquisition apparatus 2. The data acquisition apparatus 2 acquires the sensor information stored in the sensor module 1. The patient PA-specific wearing tendency is calculated on the basis of the taken-out sensor information. The condition of an alignment of teeth checked by the dentist is reflected in the calculation result of the wearing tendency, and the orthodontic design system calculates treatment plan data again. Three-dimensional data of the orthodontic appliance is created on the basis of the data which has been calculated again. The orthodontic design system transfers the created three-dimensional data to the orthodontic appliance preparation system.

An orthodontic appliance creation system receives the three-dimensional data transmitted by the orthodontic design system. The orthodontic appliance creation system creates the next orthodontic appliance on the basis of the received three-dimensional data. An orthodontic appliance system performs a treatment again using the created next orthodontic appliance.

After that, the patient PA regularly visits a dentist and the above-described procedure is repeatedly performed. The treatment is terminated when a position of the tooth reaches the final position.

A case in which a patient PA in which the intraoral sensing system 100 is utilized has a developed disease and has a medical checkup in a medical clinic will be described below.

A doctor determines that the patient PA needs daily biological information until a disease develops, such as a body temperature, an exercise amount, a blood flow, a heart rate, an oxygen concentration in blood, bacteria, and the like. The doctor requests the transferring of the biological information of the patient PA from a dental clinic. Here, the biological information is biological information determined that the doctor needs the information. The dentist who receives the request of the transferring of the biological information of the patient PA acquires the biological information of the patient PA required by the doctor from the dental storage 4 by operating the terminal apparatus 3 for a dentist, and transfers the acquired biological information to the terminal apparatus 5 for a doctor.

The terminal apparatus 5 for a doctor receives the biological information transferred by the terminal apparatus 3 for a dentist. The doctor who has received the biological information formulates a treatment plan and a treatment method on the basis of a change over time of the biological information of the patient PA.

Although a case in which the doctor determines that the biological information before the disease develops is necessary in a medical clinic in which the patient PA receive a medical treatment has been described in the flowchart shown in FIG. 7, the present invention is not limited to this example. For example, in a dental clinic, digital data required for treatment of a disease of the patient PA may be extracted from the digital data acquired from the sensor information response and the analysis may be performed using the extracted digital data, the date and time information regarding starting of sensing associated with the extracted digital data, and the information indicating a measurement time interval so that a determination concerning whether the patient PA is suspected of having a disease is performed. Furthermore, when it is determined that the patient PA is suspected of having a disease, the dental clinic may inform the medical clinic that the patient PA is suspected of having a disease. An example of processing in this case will be described.

Figure 8:
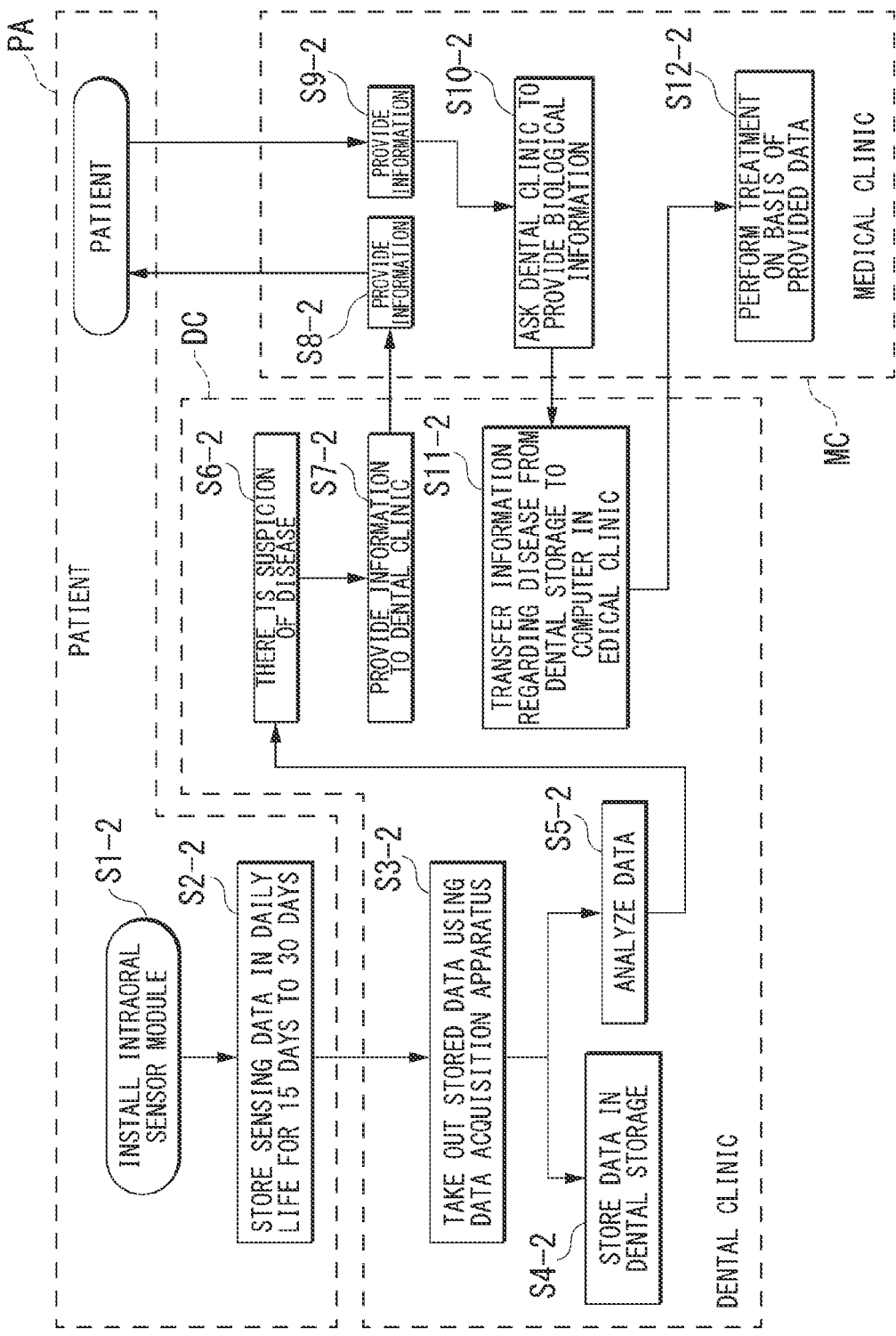
FIG. 8 is a flowchart showing a second example of the operation of the intraoral sensing system according to the present embodiment.

FIG. 8 is a flowchart showing a second example of the operation of the intraoral sensing system in this embodiment.

For the process of Step S1-2 to Step S3-2, Step S1-1 to Step S3-1 of FIG. 7 can be applied.

Although not shown in the drawings, after the process of Step S3-1, the same processing as in Step S4-1 of FIG. 7 is performed. To be specific, the terminal apparatus 3 for a dentist creates sensor information request on the basis of an operation of a user such as a dentist, and transmits the created sensor information request to the data acquisition apparatus 2. The data acquisition apparatus 2 creates the sensor information response on the basis of the sensor information request transmitted by the terminal apparatus 3 for a dentist. The data acquisition apparatus 2 transmits the created sensor information response to the terminal apparatus 3 for a dentist.

The terminal apparatus 3 for a dentist receives the sensor information response transmitted by the data acquisition apparatus 2 in response to the sensor information request. The terminal apparatus 3 for a dentist acquires date and time information regarding starting of sensing, information indicating a measurement time interval, a patient ID, the ID of the sensor module 1, a measurement index, and digital data, each included in the received sensor information response. The terminal apparatus 3 for a dentist extracts digital data required for the dental treatment of the patient PA from the acquired digital data. The terminal apparatus 3 for a dentist performs analysis required for the dental treatment on the basis of the extracted digital data, the date and time information regarding starting of sensing associated with the extracted digital data, and information indicating a measurement time interval. For example, the terminal apparatus 3 for a dentist calculates a time at which the patient PA wears an orthodontic appliance from temperature information or calculates the number of chewing of the patient PA from acceleration information. After that, the process proceeds to the process of Step S1-1.

From the results analyzed using the terminal apparatus 3 for a dentist, a dentist formulates a treatment plan for a prescribed period such as for the next 15 days to 30 days. The patient PA wears the sensor module 1 in the oral cavity again and acquires digital data in daily life for a prescribed period such as for 15 days to 30 days. After that, this is repeatedly performed.

(Step S4-2) The data acquisition apparatus 2 stores the received sensor information in the dental storage 4.

(Step S5-2) The terminal apparatus 3 for a dentist creates sensor information request on the basis of an operation of a user such as a dentist, and transmits the created sensor information request to the data acquisition apparatus 2.

The data acquisition apparatus 2 creates sensor information response on the basis of the sensor information request transmitted by the terminal apparatus 3 for a dentist. The data acquisition apparatus 2 transmits the created sensor information response to the terminal apparatus 3 for a dentist.

(Step S6-2) The terminal apparatus 3 for a dentist receives the sensor information response transmitted by the data acquisition apparatus 2 in response to the sensor information request. The terminal apparatus 3 for a dentist acquires a patient ID, date and time information regarding starting of sensing, information indicating a measurement time interval, the ID of the sensor module 1, a measurement index, and digital data, each included in the received sensor information response. The processing unit 32 of the terminal apparatus 3 for a dentist performs analysis using the acquired digital data, the date and time information regarding starting of sensing associated with the digital data, and information indicating a measurement time interval. The processing unit 32 determines whether there is a suspicion of a disease on the basis of the analysis result. When it determined that there is no suspicion of a disease, the process is terminated.

(Step S7-2) When it is determined in the terminal apparatus 3 for a dentist that there is a suspicion of a disease, the processing unit 32 creates disease information destined for the terminal apparatus 5 for a doctor, which includes a name of a patient and a disease name of the suspected disease. The processing unit 32 outputs the created disease information to the communication unit 31. The communication unit 31 acquires the disease information output by the processing unit 32 and transmits the acquired disease information to the terminal apparatus 5 for a doctor. When notifying the terminal apparatus 5 for a doctor of the disease information, the processing unit 32 associates a patient ID, a disease name of the suspected disease, a date and time at which a disease has developed, and a name of a medical clinic MC in which a notification is provided with each other, and stores the association in the dental storage 4.

(Step S8-2) The terminal apparatus 5 for a doctor receives the disease information transmitted by the terminal apparatus 3 for a dentist. A communication for recommending to have a medical checkup is sent from the medical clinic to the patient PA included in the disease information.

(Step S9-2) The patient PA who received a recommendation to have a medical checkup from the medical clinic MC has the medical checkup in the medical clinic MC.

For Step S10-2 to Step S12-2, Step S9-1 to Step S11-1 of FIG. 7 can be applied.

According to a flow shown in FIG. 8, a dental clinic DC can determine whether there is a suspicion of a disease from the biological information of the patient PA. For this reason, the dentist can notify a doctor that the patient PA is likely to develop a disease at a pre-illness stage in which a disease of the patient PA has not developed yet.

Also, for example, it may be arranged such that in the dental clinic DC, digital data required for the treatment of the disease of the patient PA be extracted from the digital data acquired from the sensor information response; and the analysis be performed using the extracted digital data, the date and time information regarding starting of sensing associated with the extracted digital data, and information indicating a measurement time interval so that a determination concerning whether the patient PA is suspected of having a disease is performed. Furthermore, when the patient PA is suspected of having a disease, the dental clinic DC may inform the patient PA that there is a suspicion of a disease. An example of processing in this case will be described.

Figure 9:
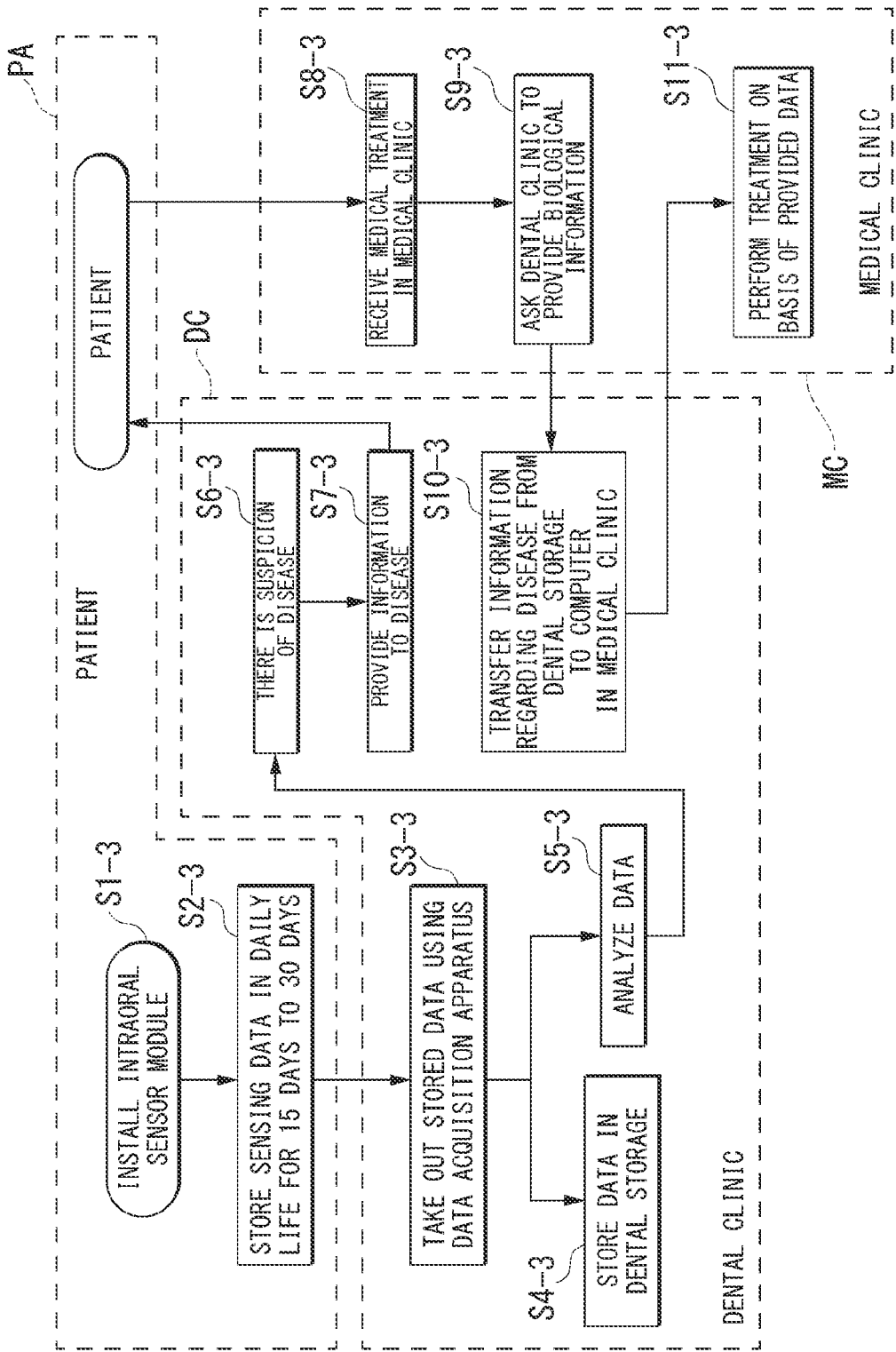
FIG. 9 is a flowchart showing a third example of the operation of the intraoral sensing system according to the present embodiment.

FIG. 9 is a flowchart showing a third example of the operation of the intraoral sensing system in this embodiment.

For Step S1-3 to Step S3-3, Step S1-1 to Step S3-1 of FIG. 7 can be applied, and for Step S4-3 to Step S6-3, Step S4-2 to Step S6-2 of FIG. 8 can be applied.

(Step S7-3) In the dental clinic DC, when it is determined that there is a suspicion of a disease, the processing unit 32 notifies the patient PA that there is a suspicion of the disease.

(Step S8-3) The patient PA who received a notification in which there was a suspicion of the disease from the dental clinic DC has a medical checkup in the medical clinic MC.

For Step S9-3 to Step S11-3, Step S9-1 to Step S11-1 of FIG. 7 can be applied.

According to a flow shown in FIG. 9, a dental clinic can determine whether the patient PA is suspected of having a disease from the biological information. For this reason, the dentist can notify the patient PA that the patient PA is likely to develop a disease at a pre-illness stage in which a disease of the patient PA has not developed.

Although a case in which the sensor information is transmitted from the sensor module 1 to the data acquisition apparatus 2 and the sensor information is transmitted from the data acquisition apparatus 2 to one or both of the terminal apparatus 3 for a dentist and the dental storage 4 has been described in the above-described embodiment, the present invention is not limited to this example. For example, the sensor information may be transmitted from the sensor module 1 to the dental storage 4. With such a constitution, the terminal apparatus 3 for a dentist can acquire the sensor information stored in the sensor module 1 without using the data acquisition apparatus 2. An example of processing in this case will be described.

Figure 10:
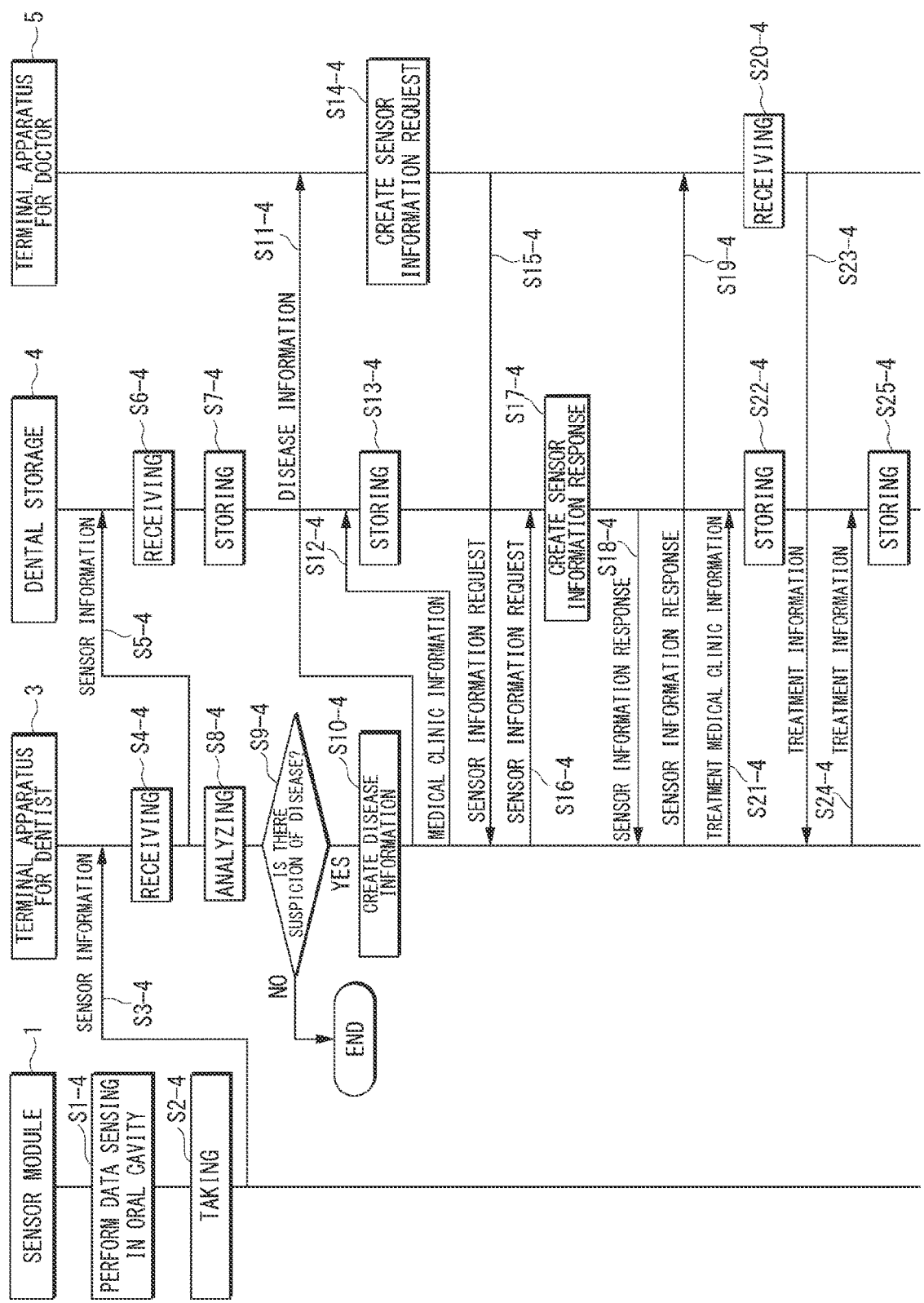
FIG. 10 is a flowchart showing a fourth example of the operation of the intraoral sensing system according to the present embodiment.

FIG. 10 is a flowchart showing a fourth example of the operation of the intraoral sensing system in this embodiment. FIG. 10 shows the operation after the initial setting of the sensor module 1 is completed and the sensor module 1 is installed in the oral cavity.

For Step S1-4, Step S2-1 of FIG. 7 can be applied.

(Step S2-4) After a prescribed period has elapsed, the patient PA visits the dental clinic DC. A dentist takes out the sensor module 1.

The terminal apparatus 3 for a dentist creates sensor information acquisition request on the basis of an operation of a user such as a dentist, and transmits the created sensor information acquisition request to the sensor module 1.

In the sensor module 1, the wireless transmission/reception unit 16 receives the sensor information acquisition request transmitted by the terminal apparatus 3 for a dentist.

(Step S3-4) In the sensor module 1, the signal processing unit 14 acquires the sensor information acquisition request received by the wireless transmission/reception unit 16, and creates sensor information destined for the terminal apparatus 3 for a dentist, which includes the information acquired by associating the date and time information regarding starting of sensing, the information indicating a measurement time interval, the patient ID, the ID of the sensor module 1, the measurement index, and the digital data with each other stored in the memory 15, on the basis of the acquired sensor information acquisition request. The signal processing unit 14 outputs the created sensor information to the wireless transmission/reception unit 16. The wireless transmission/reception unit 16 acquires the sensor information output by the signal processing unit 14, and transmits the acquired sensor information to the terminal apparatus 3 for a dentist.

(Step S4-4) The terminal apparatus 3 for a dentist receives the sensor information transmitted by the sensor module 1.

(Step S5-4) The terminal apparatus 3 for a dentist transmits the received sensor information to the dental storage 4.

(Step S6-4) The dental storage 4 receives the sensor information transmitted by the terminal apparatus 3 for a dentist.

(Step S7-4) The dental storage 4 associates the date and time information regarding starting of sensing, the information indicating a measurement time interval, the patient ID, the ID of the sensor module 1, the measurement index, and the digital data, each included in the received sensor information with each other, and stores the association.

(Step S8-4) In the terminal apparatus 3 for a dentist, the processing unit 32 acquires the sensor information received by the communication unit 31, and obtains the date and time information regarding starting of sensing, the information indicating a measurement time interval, the patient ID, the ID of the sensor module 1, the measurement index, and the digital data, each included in the acquired sensor information. The processing unit 32 performs analysis using the acquired digital data, the date and time information regarding starting of sensing and associated with the digital data, and the information indicating a measurement time interval. To be specific, in the terminal apparatus 3 for a dentist, as shown in Step S4-1 of FIG. 7, the processing unit 32 performs the analysis of the dental treatment. Furthermore, the terminal apparatus 3 for a dentist analyzes the suspicion of a medical disease. In the terminal apparatus 3 for a dentist, at the time of analyzing the suspicion of a medical disease, the processing unit 32 analyzes the medical disease by analyzing what kind of medical disease is suspected based on the sensor information using a medical disease database or a learned artificial intelligence capable of analyzing a medical disease.

(Step S9-4) In the terminal apparatus 3 for a dentist, the processing unit 32 determines whether the patient PA is suspected of having a disease on the basis of the analysis result. When it is determined that there is no suspicion of a disease, the process is terminated.

(Step S10-4) In the terminal apparatus 3 for a dentist, when it is determined that the patient PA is suspected of having a disease, the processing unit 32 creates disease information destined for the terminal apparatus 5 for a doctor, which includes the patient ID of the patient PA and the information indicating that there is a suspicion of a disease.

(Step S11-4) In the terminal apparatus 3 for a dentist, the processing unit 32 outputs created disease information to the communication unit 31. The communication unit 31 acquires the disease information output by the processing unit 32, and transmits the acquired disease information to the terminal apparatus 5 for a doctor.

(Step S12-4) In the terminal apparatus 3 for a dentist, the processing unit 32 creates medical clinic information destined for the dental storage 4, which includes information indicating contact information of the medical clinic MC corresponding to the terminal apparatus 5 for a doctor having notified of disease information, a patient ID, a name of a disease which is likely to develop, and information indicating a date and time at which the disease has developed. The processing unit 32 outputs the created medical clinic information to the communication unit 31. The communication unit 31 transmits the medical clinic information output by the processing unit 32 to the dental storage 4.

(Step S13-4) In the dental storage 4, the communication unit 41 receives the medical clinic information transmitted by the terminal apparatus 3 for a dentist. The processing unit 42 acquires information indicating contact information of the medical clinic MC, a patient ID, a name of a disease which is likely to develop, and information indicating a date and time at which the disease has developed, each included in the medical clinic information received by the communication unit 41. The processing unit 42 stores the information indicating the acquired contact information of the medical clinic MC, the name of a disease which is likely to develop, and the information indicating a date and time at which the disease has developed, in association with the same patient ID as the acquired patient ID among the patient IDs stored in the storage unit 45.

(Step S14-4) In the terminal apparatus 5 for a doctor, the communication unit 51 receives the disease information transmitted by the terminal apparatus 3 for a dentist. The processing unit 52 acquires the disease information received by the communication unit 51, and recommends the patient PA to receive a medical treatment in the medical clinic MC on the basis of the name of the patient PA included in the acquired disease information.

The patient PA who has received a recommendation of the reception of a medical treatment in the medical clinic MC has a medical checkup in the medical clinic MC. A doctor determines that sensor information is necessary.

The doctor asks the dental clinic DC to provide biological information. To be specific, the terminal apparatus 5 for a doctor creates a request for sensor information destined for the terminal apparatus 3 for a dentist, which includes a name of the patient PA, a disease name, and information indicating an information provision period, on the basis of an operation of a user such as a doctor.

(Step S15-4) The terminal apparatus 5 for a doctor transmits the created sensor information request to the terminal apparatus 3 for a dentist.

(Step S16-4) In the terminal apparatus 3 for a dentist, the communication unit 31 receives the sensor information request transmitted by the terminal apparatus 5 for a doctor. The processing unit 32 specifically identifies a patient ID corresponding to the name of the patient PA included in the sensor information request received by the communication unit 31, and specifically identifies the required biological information on the basis of the disease name. The processing unit 32 outputs the sensor information request destined for the dental storage 4, which includes the specifically identified patient ID and the biological information, to the communication unit 31. The communication unit 31 acquires the sensor information request output by the processing unit 32, and transmits the acquired sensor information request to the dental storage 4.

(Step S17-4) In the dental storage 4, the communication unit 41 receives the sensor information request transmitted by the terminal apparatus 3 for a dentist. The processing unit 42 acquires the sensor information request received by the communication unit 41. The processing unit 42 acquires the patient ID and the biological information included in the acquired sensor information request, and acquires information corresponding to the acquired biological information, date and time information regarding starting of sensing, information indicating a measurement time interval, the ID of the sensor module 1, and a measurement index, among the digital data stored in association with the same patient ID as the acquired patient ID, from the storage unit 45. The processing unit 42 creates a response for sensor information destined for the terminal apparatus 3 for a dentist, which includes the patient ID, the acquired digital data, the date and time information regarding starting of sensing, the information indicating a measurement time interval, the ID of the sensor module 1, and the measurement index.

(Step S18-4) In the dental storage 4, the processing unit 42 outputs the created sensor information response to the communication unit 41. The communication unit 41 acquires the sensor information response output by the processing unit 42 and transmits the acquired sensor information response to the terminal apparatus 3 for a dentist.

(Step S19-4) In the terminal apparatus 3 for a dentist, the communication unit 31 receives the sensor information response transmitted by the dental storage 4. The processing unit 32 acquires the sensor information response received by the communication unit 31. The processing unit 32 calculates each measurement date and time of the digital data on the basis of the date and time information regarding starting of sensing, the information indicating a measurement time interval, the measurement index, and the digital data, each included in the acquired sensor information response. Furthermore, the processing unit 32 specifically identifies the name of the patient PA corresponding to the patient ID. The processing unit 32 creates a response of sensor information destined for the terminal apparatus 5 for a doctor, which includes the specifically identified name of a patient, a disease name, a measurement date and time, and digital data. The processing unit 32 outputs the created sensor information response to the communication unit 31. The communication unit 31 transmits the sensor information response output by the processing unit 32 to the terminal apparatus 5 for a doctor.

(Step S20-4) In the terminal apparatus 5 for a doctor, the communication unit 51 receives the sensor information response transmitted by the terminal apparatus 3 for a dentist. The processing unit 52 acquires the sensor information response received by the communication unit 51. The processing unit 52 outputs the name of a patient, the disease name, the measurement date and time, and the digital data, each included in the acquired sensor information response.

A doctor reflects the name of a patient, the disease name, the measurement date and time, and the digital data, each output by the terminal apparatus 5 for a doctor in the treatment.

(Step S21-4) In the terminal apparatus 3 for a dentist, the processing unit 32 specifically identifies the patient ID corresponding to the name of a patient and the ID of the sensor module 1 included in the sensor information response transmitted to the terminal apparatus 5 for a doctor. The processing unit 32 creates treatment medical clinic information destined for the dental storage 4, which includes a patient ID, a disease name, a developed date and time, and a medical clinic name in which a sensor information response has been transmitted. The processing unit 32 outputs the created treatment medical clinic information to the communication unit 31. The communication unit 31 acquires the treatment medical clinic information output by the processing unit 32, and transmits the acquired medical clinic information to the dental storage 4.

(Step S22-4) In the dental storage 4, the communication unit 41 receives the treatment medical clinic information transmitted by the terminal apparatus 3 for a dentist. The processing unit 42 acquires a patient ID, a disease name, a developed date and time, and a name of a medical clinic to which a sensor information response is transmitted, each included in the treatment medical clinic information received by the communication unit 41. The processing unit 42 stores the acquired disease name, the developed date and time, and the name of the medical clinic to which the sensor information response is transmitted in association with the same patient ID as the acquired patient ID among the patient IDs stored in the storage unit 45.

(Step S23-4) In the terminal apparatus 5 for a doctor, the processing unit 52 creates treatment information destined for the terminal apparatus 3 for a dentist, which includes a name of the patient PA, a disease name, information indicating a developed date and time, a medical clinic name, and treatment information, on the basis of an operation of a user such as a doctor. The processing unit 52 outputs the created treatment information to the communication unit 51. The communication unit 51 creates the treatment information output by the processing unit 52 and transmits the created treatment information to the terminal apparatus 3 for a dentist.

(Step S24-4) In the terminal apparatus 3 for a dentist, the communication unit 31 receives the treatment information transmitted by the terminal apparatus 5 for a doctor. The processing unit 32 specifically identifies a patient ID corresponding to the name of the patient PA included in the treatment information received by the communication unit 31. The processing unit 32 creates treatment information destined for the dental storage 4, which includes the specifically identified patient ID, the disease name, the information indicating the developed date and time, the medical clinic name, and the treatment information. The processing unit 32 outputs the created treatment information to the communication unit 31. The communication unit 31 acquires the treatment information output by the processing unit 32, and transmits the acquired treatment information to the dental storage 4.

(Step S25-4) In the dental storage 4, the communication unit 41 receives the treatment information transmitted by the terminal apparatus 3 for a dentist. The processing unit 42 acquires a patient ID, a disease name, information indicating a developed date and time, a medical clinic name, and treatment information, included in the treatment information received by the communication unit 41. The processing unit 42 stores the acquired disease name, information indicating a developed date and time, medical clinic name, and treatment information, in association with the same patient ID as the acquired patient ID among the patient IDs stored in the storage unit 45.

Although a case in which the data acquisition apparatus 2, the terminal apparatus 3 for a dentist, the dental storage 4, and the terminal apparatus 5 for a doctor are connected over the network NW has been described in the above-described embodiment, the present invention is not limited to this example. For example, each of the data acquisition apparatus 2, the dental storage 4, and the terminal apparatus 5 for a doctor may be connected to the terminal apparatus 3 for a dentist in a wired manner. When the data acquisition apparatus 2, the terminal apparatus 3 for a dentist, the dental storage 4, and the terminal apparatus 5 for a doctor are connected over the network NW, even when the patient PA has gone to a remote location, a dentist or a doctor can access digital data of the patient PA. For this reason, this can significantly contribute to the treatment of the disease of the patient PA.

Although a case in which the sensor module 1 and the data acquisition apparatus 2 are connected wirelessly has been described in the above-described embodiment, the present invention is not limited to this example. For example, the sensor module 1 and the data acquisition apparatus 2 may be connected in a wired manner. In this case, the sensor module unit 13 includes a module configured to perform transmission and reception in a wired manner instead of the wireless transmission/reception unit 16. When a module configured to perform transmission and reception in a wired manner is provided, a connector part configured to connect the sensor module 1 to the data acquisition apparatus 2 needs to have a waterproof structure. As an example of a waterproof mechanism, an opening/closing mechanism such as a lid is installed on a connector part. The opening/closing mechanism opens when digital data is read from the sensor module 1 to the data acquisition apparatus 2, and closes when the sensor module 1 is installed in the oral cavity. When the sensor module 1 and the data acquisition apparatus 2 are connected wirelessly, a waterproof structure can be simplified.

Although a case in which the sensor module 1 is installed in the implant IN has been described in the above-described embodiment, the present invention is not limited to this example. For example, the same applies to a case in which the sensor module 1 is installed in the denture. When the sensor module 1 is installed in the denture, the sensor module 1 is installed in the denture. When the sensor module 1 is installed in the denture and at least one of a pulse wave sensor configured to measure pulse waves using light, a pulse oximeter configured to measure an oxygen concentration in blood using light, a heart rate sensor configured to measure a heart rate using light, and a laser sensor configured to measure a blood flow using laser light is installed in the sensor module 1, information is acquired from the blood vessels of the gum portion. Thus, it is desirable that the sensor module 1 be installed in the gum.

Also, when the sensor module 1 has a sensor installed therein in which light or a laser is utilized, the transmission of light is essential. Thus, at least a part of the denture needs to be made of a material through which any wavelength of light with 400 nm to 1000 nm can be transmitted.

In the above-described embodiment, the terminal apparatus 3 for a dentist may have an analysis program configured to derive a disease which is likely to develop from a daily change in biological information. The dental storage 4 has the disease name of the patient PA and the daily change in biological information of the patient PA presented from a doctor or a dentist accumulated therein. The terminal apparatus 3 for a dentist can estimate a disease of the patient PA which is likely to develop from the change in biological information through deep learning of the disease name of the patient PA and the daily change in biological information of the patient PA. With such a constitution, since the terminal apparatus 3 for a dentist automatically picks up a disease of the patient PA which is likely to develop, the dentist can acquire the disease of the patient PA without sequentially checking daily biological information of the patient PA. For this reason, the risk of doctor oversight can be reduced.

According to the intraoral sensing system 100 in this embodiment, the sensor module 1 including the sensor 12 is installed in the denture, the implant, and the orthodontic appliance required for the treatment of the oral cavity which are required for daily life. With such a constitution, in addition to the biological information intended for the original dental treatment, biological information of daily life can be obtained separately from dental treatment. For this reason, it is possible to ascertain a change in biological information of daily life of the patient PA. So far, only after getting some kind of illness, the patient PA starts to acquire his/her biological information regarding the illness. Thus, it was difficult to determine whether the information is due to illness or the individual characteristics of the patient.

However, according to the intraoral sensing system 100, biological information can be acquired from the sensor module 1 installed in the orthodontic appliance, the denture, and the implant which are utilized daily. Thus, the terminal apparatus 5 for a doctor can analyze a change in biological information by acquiring the biological information acquired by the sensor module 1. Accordingly, it can significantly contribute to the treatment of illness.

According to the intraoral sensing system 100 in this embodiment, it is possible to acquire biological information in chronological order. Thus, it is possible to read the change in biological information of the patient PA. So far, only after the patient PA getting some kind of illness, biological information regarding the illness was obtained. Thus, only biological information at the time of measurement was be able to be obtained.

According to the intraoral sensing system 100 in this embodiment, it is possible to acquire daily biological information by installing the sensor module 1 including the sensor 12 in an apparatus used for oral treatment such as an orthodontic appliance, a denture, and an implant. For this reason, it is possible to establish medical cooperation between dentistry and medicine, and to elucidate the developing process of a disease. For this reason, a significant transformation can be provided in medical diagnosis. So far, the biological information required for dental treatment is measured at a dental clinic and data required for medical treatment is measured at a medical clinic by installing a sensor.

According to the intraoral sensing system 100 in this embodiment, when a time at which an orthodontic appliance is worn is measured using the temperature sensor utilized in the sensor 12, the intraoral sensing system 100 can be utilized not only for oral orthodontic treatment but also for monitoring a daily change in body temperature.

According to the intraoral sensing system 100 in this embodiment, in addition to the fact that the number of chewing can be counted, the number of walking steps, an amount of activity, the movement of the jaw, bruxism (gnashing), and the number of times of chewing and swallowing can be measured using the acceleration sensor and the gyro sensor as the sensor 12.

According to the intraoral sensing system 100 in this embodiment, in addition to the fact that a force applied to teeth, dentures, and implant can be measured, a force applied to the teeth by the orthodontic appliance, bruxism (gnashing), a chewing force, the number of chewing, and a time at which the orthodontic appliance is worn can be measured using the pressure sensor and the strain sensor as the sensor 12.

According to the intraoral sensing system 100 in this embodiment, since the sensor module 1 includes the wireless transmission/reception unit 16, it is possible to transmit sensor information to the outside without providing a connector configured to read digital data in the sensor module 1. Since it is not necessary to provide a connector in the sensor module 1, a waterproof structure configured to fully cover the sensor module 1 can be adopted. When a connector configured to read digital data is provided in the sensor module 1 and sensor information is transmitted to the outside in a wired manner, since the sensor module 1 is installed in the oral cavity, the waterproof configuration needs to be provided. In this case, normally, an opening/closing mechanism such as a lid is installed in a connector portion, and a mechanism in which the opening/closing mechanism opens when digital data is read and closes when the connector portion is installed in the oral cavity are adopted. Since the sensor module 1 to be installed in the oral cavity is very small, applying of a mechanism of a waterproof lid is technically difficult.

According to the intraoral sensing system 100 in this embodiment, since the sensor module 1 includes the memory 15, it is possible to store the digital data sensed by the sensor 12. Furthermore, when the orthodontic appliance, the denture, or the implant is removed from the oral cavity, the digital data stored in the memory 15 can be transmitted to the outside. For this reason, time series data can be acquired without any omission in time. When the sensor module 1 is not provided with the memory 15, it is necessary to wirelessly transmit the digital data sensed by the sensor 12 to the outside without storing the digital data. In addition, since the sensor module 1 is installed in the oral cavity, it is difficult for radio waves to go outside of the oral cavity and there is a concern that the data may not be transmitted.

Also, when data is transmitted wirelessly at each time sensing is performed, the energy consumption of the battery increases. According to the intraoral sensing system 100 in this embodiment, when the orthodontic appliance, the denture, or the implant is removed from the oral cavity, the digital data stored in the memory 15 can be transmitted wirelessly so that the energy consumption of the battery can be reduced. Accordingly, it is possible to extend the lifespan of battery energy.

Modified Example of Embodiment

A modified example of the embodiment will be described below with reference to the drawings. Constituent elements having the same or similar functions are denoted by the same reference numerals and duplicate description regarding the constitutions will be omitted in some cases.

Although the digital data is stored in the memory 15 of the sensor module 1 in the embodiment, it is difficult for the patient PA to confirm whether the sensor module 1 is operating. In the modified example of the embodiment, the patient PA can confirm whether the sensor module 1 is operating.

(Intraoral Sensing System)

Figure 11:
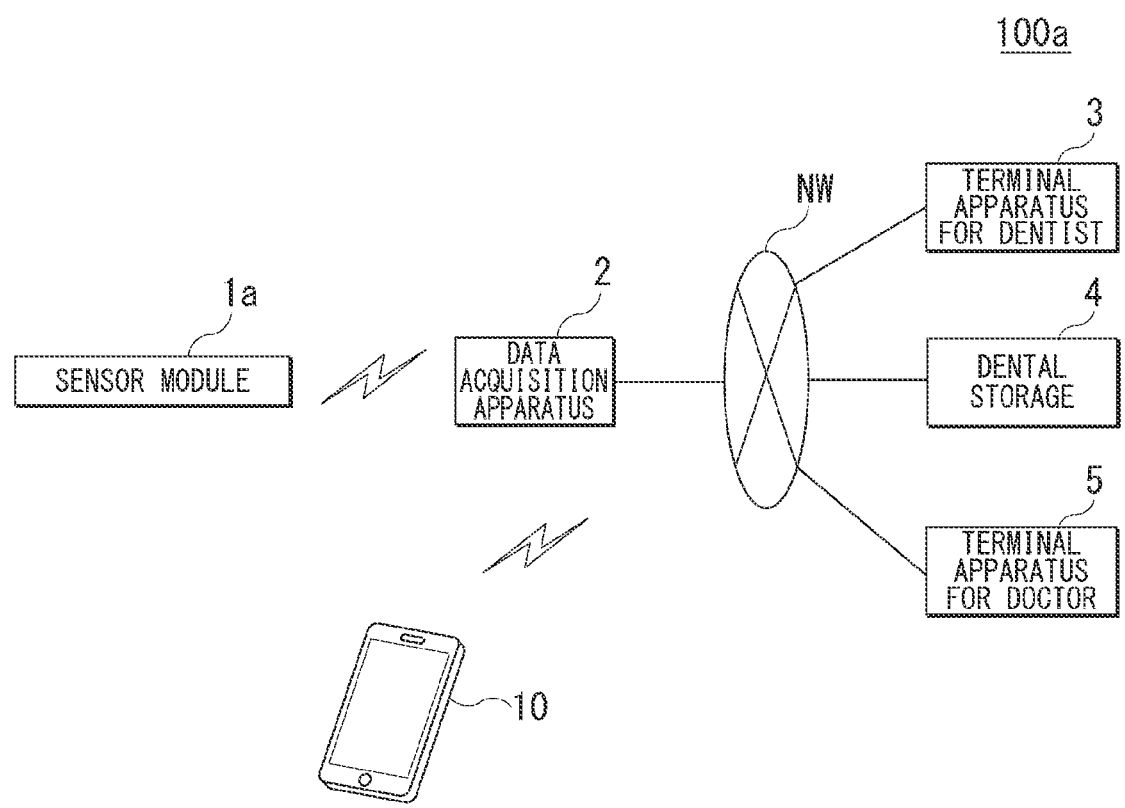
FIG. 11 is a diagram showing an example of an intraoral sensing system according to a modified example of the present embodiment.

FIG. 11 is a diagram showing an example of an intraoral sensing system according to a modified example of the embodiment of the present invention. An intraoral sensing system 100*a* of the modified example of the embodiment of the present invention senses biological information using a sensor module installed in the oral cavity.

The intraoral sensing system 100*a* includes a sensor module 1*a*, a data acquisition apparatus 2, a terminal apparatus 3 for a dentist, a dental storage 4, a terminal apparatus 5 for a doctor, and a terminal apparatus 10.

The sensor module 1*a* creates a confirmation signal for providing a notification that the sensor module 1*a* is operating, and wirelessly transmits the created confirmation signal.

The terminal apparatus 10 is carried by, for example, a patient PA who wears the sensor module 1*a*. The terminal apparatus 10 receives the confirmation signal wirelessly transmitted by the sensor module 1*a*. The terminal apparatus 10 outputs information indicating that the confirmation signal has been received when receiving the confirmation signal. The terminal apparatus 10 confirms the operation of the sensor module 1*a* by receiving the operation confirmation signal transmitted by the sensor module 1*a*.

The sensor module 1*a* and the terminal apparatus 10 of the intraoral sensing system 100*a* in the modified example of the embodiment of the present invention which are different from those of the embodiment will be described.

Figure 12:
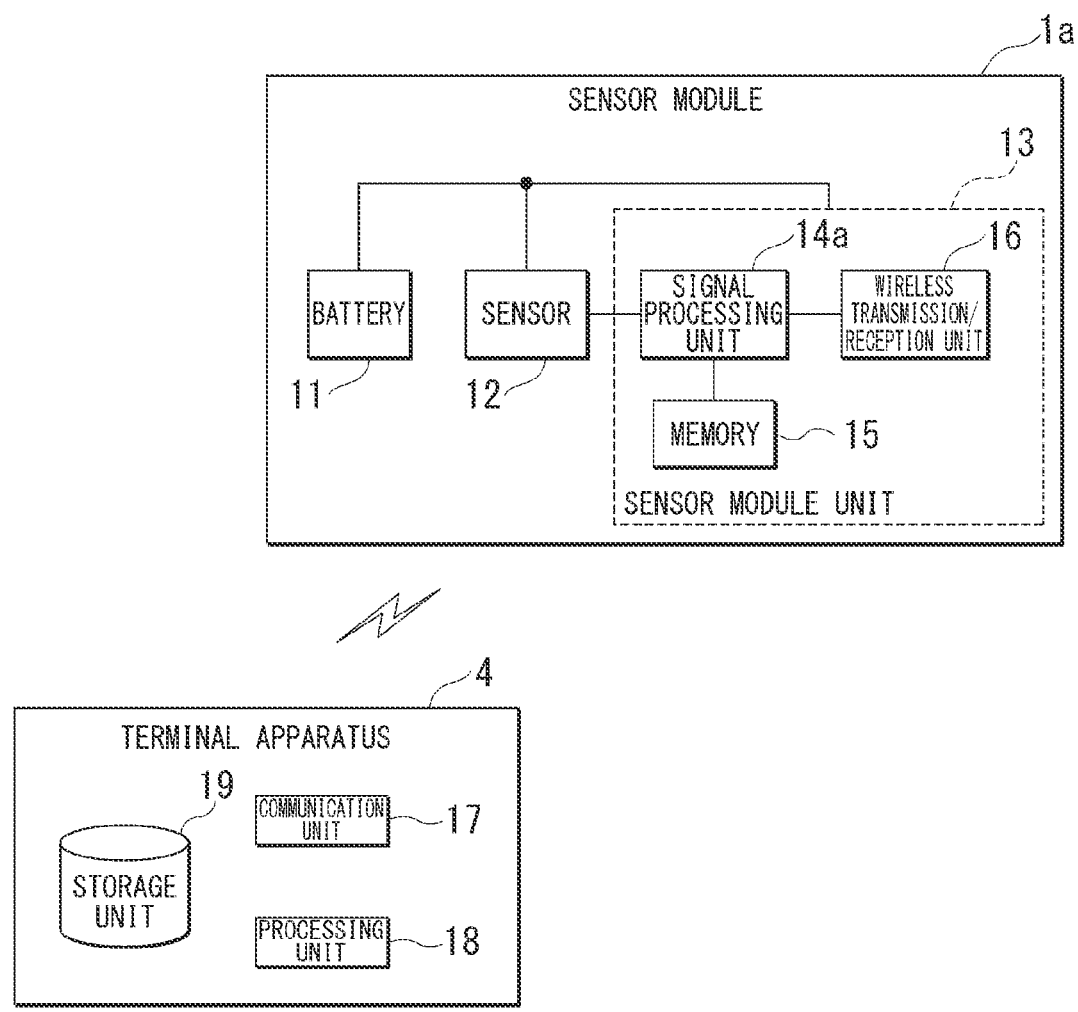
FIG. 12 is a block diagram showing a sensor module constituting the intraoral sensing system according to the modified example of the present embodiment, and a terminal apparatus.

FIG. 12 is a block diagram showing the sensor module and the terminal apparatus constituting the intraoral sensing system in the modified example of the embodiment.

(Sensor Module 1*a*)

For the sensor module 1*a*, a sensor module 1 can be applied. Here, the sensor module 1*a* and the sensor module 1 differ in that a signal processing unit 14*a* is provided instead of the signal processing unit 14.

For the signal processing unit 14*a*, the signal processing unit 14 can be applied. Here, the signal processing unit 14*a* creates a confirmation signal and outputs the created confirmation signal to a wireless transmission/reception unit 16.

The wireless transmission/reception unit 16 wirelessly transmits the confirmation signal output by the signal processing unit 14*a*.

(Terminal Apparatus 10)

The terminal apparatus 10 is implemented using an apparatus such as a personal computer, a smartphone, a tablet computer, or the like. The terminal apparatus 10 includes, for example, a communication unit 17, a processing unit 18, and a storage unit 19.

The communication unit 17 is implemented using a communication module. The communication unit 17 communicates with an external communication apparatus. The communication unit 17 may communicate through a communication method such as a BLE. The communication unit 17 holds communication information required for communicating with the sensor module 1a. The communication unit 17 receives the confirmation signal transmitted by the sensor module 1a.

The storage unit 19 is implemented using an HDD, a flash memory, a RAM, a ROM, or the like.

The processing unit 18 is realized using a computer program (software) stored in a storage unit 19 and executed by a hardware processor such as a CPU. Furthermore, some or all of these functional units may be implemented using hardware (circuit units; including circuitries) such as a large scale integration (LSI), an application specific integrated circuit (ASIC), a field-programmable gate array (FPGA), and a graphics processing unit (GPU), or may be realized through the cooperation of software and hardware. The computer program may be stored in a storage apparatus such as hard disk drives (HDDs) and flash memories in advance, or may be stored in an attachable/detachable storage medium such as DVDs and CD-ROMs so as to be installed when a storage medium is installed in a drive apparatus.

The processing unit 18 receives the confirmation signal received by the communication unit 17. The processing unit 18 outputs information indicating the acquisition of the confirmation signal on the basis of the acquired confirmation signal. Here, the processing unit 18 may output the information indicating the acquisition of the confirmation signal to a display unit (not shown) or output a sound from a speaker (not shown).

Although a case in which the sensor module 1a transmits the confirmation signal has been described in the above-described modified example of the embodiment, the present invention is not limited to this example. For example, the sensor module 1a may transmit a beacon signal including prescribed information such as digital data and data indicating a processed wearing time. In this case, the terminal apparatus 10 may ascertain whether the sensor module 1 is operating by receiving the beacon signal transmitted by the sensor module 1a.

Also, for example, the sensor module 1a may transmit a beacon signal including prescribed information and the terminal apparatus 10 may receive the beacon signal without transmitting and receiving wireless data between the sensor module 1a and the terminal apparatus 10. With such a constitution, the power consumption of the sensor module 1a can be reduced.

According to the intraoral sensing system 100a in the modified example of the embodiment, the sensor module 1a transmits an operation confirmation signal and the terminal apparatus 10 receives the operation confirmation signal transmitted by the sensor module 1a. With such a constitution, a person who carries the terminal apparatus 10 such as a patient PA can know whether the sensor module 1a is operating. Although the digital data is stored in the memory 15 of the sensor module 1, it is difficult for the patient PA to confirm whether the sensor module 1 is operating, but the operation confirmation signal is transmitted from the wireless transmission/reception unit and the patient PA can know an operation state of the sensor module when a mobile terminal possessed by the patient PA receives the signal.

Although the embodiments of the present invention have been described above, these embodiments are presented as examples and are not intended to limit the scope of the present invention. The embodiments can be implemented in various other forms and various omissions, replacements, and changes are possible without departing from the gist of the present invention. The embodiments and the modifications thereof include, for example, those that can be easily assumed by those skilled in the art, those that are substantially the same, those that have an equal range, and the like.

For example, a computer program configured to realize the functions of the above-described apparatuses may be recorded on a computer-readable recording medium and the computer program recorded on the recording medium may be read in the computer system and executed. The "computer system" mentioned herein may include hardware such as an OS and peripheral apparatuses.

Also, a "computer-readable recording medium" is a flexible disk, a magneto-optical disk, a ROM, a writable non-volatile memory such as a flash memory, a portable medium such as a digital versatile disc (DVD), and a storage apparatus such as a hard disk built in a computer system.

Furthermore, a "computer-readable recording medium" is a medium configured to hold a program for a certain period of time such as a volatile memory (for example, a dynamic random access memory (DRAM)) inside a computer system which serves a server or a client when a computer program is transmitted via a network such as the Internet or a communication line such as a telephone line.

In addition, the program may be transmitted from a computer system in which this program is stored in a storage apparatus or the like to another computer system via a transfer medium or using transmission waves in the transfer medium. Here, the "transfer medium" configured to transfer a program refers to a medium having a function of transferring information such as a network (a communication network) such as the Internet or a communication line (a communication line) such as a telephone line.

The above program may be for realizing a part of the above-described functions. Moreover, the above program may be a so-called difference file (a difference program), which can be realize the above-described functions in combination with a program already recorded in the computer system.

What is claimed is:

1. An intraoral sensing system comprising:
   an intraoral sensor module configured to either be installed on a tooth or implanted in an oral cavity of a patient and configured to sense a biological information of the patient and store the sensed biological information of the patients in the sensor module;
   a storage apparatus operably connected to the sensor module and comprising an internal processor configured to acquire, from the sensor module, the sensed biological information of the patient and an identification of the patient, wherein the storage apparatus is operated by the internal processor to store in the storage apparatus the sensed biological information in association with the identification of the patient;
   a dentist terminal apparatus operably connected to the storage apparatus to receive the sensed biological information of the patient stored in the storage in association with the identification information of the patient, wherein the dentist terminal apparatus has a database in which a plurality of sets of biological information are stored in relation to diseases associated with the plurality of sets of biological information, and the dentist terminal apparatus is configured to analyze the sensed biological information to identify, from the dataset, a disease associated with the sensed biological information; and a doctor terminal apparatus operably connected to the dentist terminal apparatus to acquire, from the dentist terminal apparatus, the sensed biological information of the patient, who has developed a disease.

2. The intraoral sensing system according to claim 1, wherein the sensor module is installed in any one of an orthodontic appliance, a denture, or an implant.

3. The intraoral sensing system according to claim 1, wherein the sensed biological information of the patient is at least one of a body temperature of the patient, a blood flow of the patient, oxygen concentration in blood of the patient, a heart rate of the patient, bacterial infection of the patient, bruxism of patient, or the number of times of chewing and swallowing by the patient.

4. The intraoral sensing system according to claim 1, wherein the sensor module includes:
   a sensor configured to perform sensing of the biological information of a living body;
   a battery configured to supply an electric power;
   a signal processing unit configured to create digital data representative of the sensed biological information sensed by the sensor;
   a memory configured to store the digital data created by the signal processing unit; and
   a wireless transmission/reception unit configured to receive a command to acquire data transmitted by an acquisition apparatus and execute the command to transmit the digital data stored in the memory and the identification information of the patient to the acquisition apparatus.

5. The intraoral sensing system according to claim 1, wherein the sensor module includes at least one of a temperature sensor, an acceleration sensor, a gyro sensor, a pressure sensor, a strain sensor, a pulse wave sensor, a pulse oximeter, a heart rate sensor, or a laser sensor.

6. The intraoral sensing system according to claim 1, wherein:
   the sensor module is installed in any one of an orthodontic appliance, a denture, or an implant
   that is at least partially formed of a light-transmissive material that allow light having a wavelength of 400 nm to 1000 nm to pass therethrough.

7. The intraoral sensing system according to claim 1, wherein:
   the sensor module is configured to transmit an operation confirmation signal; and
   the intraoral sensing system includes a terminal apparatus configured to receive the operation confirmation signal transmitted by the sensor module.

8. The intraoral sensing system according to claim 1, wherein the dentist terminal apparatus includes a processing unit configured to perform at least one of a dental treatment analysis or a medical disease analysis for the patient using the sensed biological information.

9. The intraoral sensing system according to claim 8, wherein:
   when the patient is suspected of having a disease, the processing unit of the dentist terminal apparatus creates disease information, to be sent to the doctor terminal apparatus, which includes a patient ID of the patient and information on a suspected disease; and
   the dentist terminal apparatus includes a communication unit configured to transmit the disease information created by the processing unit of the dentist terminal apparatus to the terminal apparatus for a doctor.

10. The intraoral sensing system according to claim 1, wherein the sensor module includes a signal processing unit configured to create digital data representative of the sensed biological information.

* * * * *

UNITED STATES PATENT AND TRADEMARK OFFICE
CERTIFICATE OF CORRECTION

PATENT NO. : 11,864,873 B2
APPLICATION NO. : 17/194937
DATED : January 9, 2024
INVENTOR(S) : Yoshifumi Yoshida and Kotaro Maki Page 1 of 1

It is certified that error appears in the above-identified patent and that said Letters Patent is hereby corrected as shown below:

In the Claims

Claim 1, Line 51, delete "patients" and replace with -- patient --.

Signed and Sealed this
Twenty-seventh Day of February, 2024

Katherine Kelly Vidal
*Director of the United States Patent and Trademark Office*